US009946834B2

(12) United States Patent
Johnson et al.

(10) Patent No.: US 9,946,834 B2
(45) Date of Patent: Apr. 17, 2018

(54) APPARATUS AND METHOD FOR PROCESSING CELL CULTURE DATA

(75) Inventors: Christopher Johnson, London (GB); Marina Tarunina, Orpington (GB); Yen Choo, London (GB); Simon Lister, Knebworth (GB); Robert Merrifield, Enfield (GB)

(73) Assignee: PLASTICELL LIMITED, London (GB)

( * ) Notice: Subject to any disclaimer, the term of this patent is extended or adjusted under 35 U.S.C. 154(b) by 579 days.

(21) Appl. No.: 13/395,857

(22) PCT Filed: Sep. 21, 2010

(86) PCT No.: PCT/GB2010/001768
§ 371 (c)(1),
(2), (4) Date: May 4, 2012

(87) PCT Pub. No.: WO2011/033274
PCT Pub. Date: Mar. 24, 2011

(65) Prior Publication Data
US 2012/0208227 A1 Aug. 16, 2012

(30) Foreign Application Priority Data

Sep. 21, 2009 (GB) .................................. 0916585.3
Jul. 12, 2010 (GB) .................................. 1011722.4

(51) Int. Cl.
*G01N 33/48* (2006.01)
*G06F 19/24* (2011.01)

(52) U.S. Cl.
CPC .................................. *G06F 19/24* (2013.01)

(58) Field of Classification Search
CPC ..................................................... G06F 19/24
USPC ......................................................... 702/21
See application file for complete search history.

(56) References Cited

U.S. PATENT DOCUMENTS

| 6,001,585 | A | 12/1999 | Grammer |
| 2001/0051834 | A1 | 12/2001 | Domb et al. |
| 2003/0165808 | A1 | 9/2003 | Campbell et al. |
| 2004/0063088 | A1 | 4/2004 | Berg et al. |
| 2006/0035211 | A1* | 2/2006 | Levinson et al. ................ 435/4 |

FOREIGN PATENT DOCUMENTS

| WO | 9819161 A | 5/1998 |
| WO | 2004031369 | 4/2004 |
| WO | 2005070037 A2 | 8/2005 |
| WO | 2007023297 | 3/2007 |

OTHER PUBLICATIONS

Vazquez, J.A. et al. "Mathematical Tool for Objective Comparison of Microbial Cultures Application to Evaluation of 15 Peptones for Lactic Acid Bacteria Productions", Biochemical Engineering Journal 39 (2008) 276-287.
Thomas, R.J. et al. "Application of Process Quality Engineering Techniques to Improve the Understanding of the In Vitro Processing of Stem Cells for Therapeutic Use", Journal of Biotechnology 136 (2008) 148-155.
Japanese Office Action dated Oct. 11, 2014, Application No. 2012/529,340.
Nicewarner-Pena S R et al. "Submicrometer Metallic Barcodes" Science, American Association for the Advancement of Science,, US, vol. 294, No. 5540, Oct. 5, 2001, pp. 137-141, XP001128112 ISSN:0036-8075 abstract.
Deasy B M et al.: "Mechanisms of Muscle Stem Cell Expansion With Cytokines" Stem Cells, Alphamed press, Dayton, OH, US, Jan. 2002, pp. 50-60, XP002952762 ISSN:1066-5099 the whole document.
Greenberger J S et al: Expansion of hematopoietic stem cells in vitro as a model system for human tissue engineering The Orthopedic Clinics of North America. Jul. 2000, vol. 31, No. 3, Jul. 200, pp. 499-510, XP009073761 ISSN:0030-5898 the whole document.
R. Ian Freshney: "Culture of animal cells, A manual of basic technique, third edition" 1994, Wiley-Liss Inc., New York US XP002270293 pp. 161-166.
Mellado-Damas N et al.: "Ex-vivo expansion and maturation of CD34-Positive hematopoietic progenitors optimization of culture conditions" Leukemia Research, vol. 23, No. 11, Nov. 1999, pp. 1035-1040, XP002270289 ISSN:0145-2126 the whole document.
Zimrin A B et al: "Models of in vitro angiogenesis: endothelial cell differentiation on fibrin but not matrigel is transcriptionally dependent." Biochemical and Biophysical Research Communications. US, vol. 213, No. 2, Aug. 15, 1995, pp. 630-638, XP002270290 ISSN: 0006-291x the whole document.
Einspanier R et al: "First identification of caldesmon transcripts in bovine oviduct epithelial cells in vitro by means of an RNA differential display technique examining culture-induced expression changes." Reproduction in domestic Animals = Zuchthygiene. Germany Oct. 2001, vol. 36, No. 5, Oct. 2001, pp. 230-235, XP002270291 ISSN: 093.63-6768 the whole document.

(Continued)

*Primary Examiner* — Jerry Lin
(74) *Attorney, Agent, or Firm* — Park, Vaughan, Fleming & Dowler LLP

(57) ABSTRACT

One embodiment of the invention provides a method of processing cell culture data. The data comprises results from a large number of samples, the results being obtained by performing multiple stages of cell culture in succession on each sample. Each stage represents a cell culture treatment having a particular set of conditions, such that each sample follows a protocol specified by the identity and order of the treatments applied to the cell culture. The method includes specifying a subset of the samples that yielded a desired cell culture outcome. The method further includes performing a computer-implemented analysis of the results from the samples in the subset to produce an ordering or grouping for the results. The ordering or grouping helps to identify one or more protocols that are effective for obtaining the desired cell culture outcome. The analysis for producing the ordering or grouping utilizes information on similarities between different protocols.

15 Claims, 27 Drawing Sheets

(56) References Cited

OTHER PUBLICATIONS

Jordan FL et al: "Method for the Identification of brain Macrophages-Phagocytic Cells In-Vitro" Journal of Neuroscience Research, vol. 26, No. 1, 1990, pp. 74-82, XP008027664 ISSN: 0360-4012 the whole document.
European Patent Office; Office Action dated Jun. 16, 2017.

* cited by examiner

APPARATUS AND METHOD FOR PROCESSING CELL CULTURE DATA

FIELD OF THE INVENTION

The present invention relates to cell culture, and in particular to an apparatus and method for processing data resulting from a large number of cell culture samples.

BACKGROUND OF THE INVENTION

Over recent years, cell culture has become a core technology in the life sciences. The underlying science of cell culture is complicated, so that the effect of different treatments and growing conditions remains poorly understood. Many cell culture treatments are developed on a trial and error basis, perhaps by analogy with existing treatments. However, this approach is time-consuming, unreliable, and clearly inefficient.

Cell culture protocols which involve multiple discrete stages are particularly difficult to devise and optimise. Changing the treatment in one stage may affect the performance of a subsequent stage, so that devising optimal combinations of treatments is particularly challenging and requires large numbers of experiments. Such experiments can be performed by conventional cell culture, although methods with higher throughput such as automated cell culture are also known. These experiments may involve methods of miniaturising cell culture, such as the use of microfluidic platforms (e.g. "Differentiation-on-a-chip: A microfluidic platform for long-term cell culture studies", Anna Tourovskaia, Xavier Figueroa-Masot and Albert Folch; Lab Chip, 2005, 5, 14-19), or cell arrays. There is a need in the art for methods to analyse data produced by high throughput cell culture techniques.

EP-A 1551954 and WO2007/023297, the contents of which are incorporated herein by reference, describe a technique in which cells are cultured in a large number of different units. Each unit may be formed from a bead with cells growing on the surface or in pores. The cell units (beads) are split into different groups and each group is subjected to a particular treatment. After this first stage (round), the cell units may be optionally pooled together again, and then split once again into new groups. The new groupings are then subjected to a second round of treatments. Further rounds of pooling, splitting, and treatment may follow. The cell units are optionally tagged during the culture treatments so that at the end of the experiment it is possible to deduce the sequence of treatments applied to a given cell unit. Cell units that have reached a desired endpoint, say the development of a particular cell type as judged by a screening assay, can be identified and the sequence of treatments to which they were exposed identified.

The number of cell units in these experiments may be very large—thousands or more. Likewise, the number of possible protocol combinations of treatments (protocols) to which different cell units have been exposed may also be large. For example, if there are 10 possible treatments at each of three stages, then this gives 1000 ($10^3$) potential protocols. If the experiment involves 50,000 cell units, then on average 50 beads will be exposed to each protocol.

Results from such large scale screening experiments require validation since these typically include false-positives, where a desired result is achieved but the outcome is spurious, and also false-negatives where a cell unit that follows a potentially productive protocol does not give a positive outcome. The number of false-negatives provides some measure of the efficiency of a given protocol, which might often be rather low (10% or less).

In general, the existing approach to analysing results from these large-scale cell culture experiments is to look for protocols that produced positive results in an endpoint screen. The successful protocols are then the subject of further experiments. This follow-up work may involve testing a larger number of cell units per protocol to give better statistics for the results, or a different experimental strategy, such as performing conventional or monolayer cell culture (rather than using small beads).

This follow-up work is relatively expensive and time-consuming to perform, especially if there are many protocols that appear to require further investigation. It would be helpful for the data analysis to be able to guide the selection of subsets of protocols for further investigation, and even to be able to predict the efficiency of these protocols a priori. For example, since experiments are often performed in parallel, e.g. multiple cell units are exposed to each protocol, a protocol may be particularly suitable for follow-up work if N or more replicates are positive in an endpoint screen (where N may be chosen as 1, 2, 3 ... etc, depending on the particular circumstances).

One important goal of such experiments is to be able to control or direct the differentiation of cells towards a particular phenotype. For example, starting with stem cells, it may be desired to produce in culture a specific type of cell, for example red blood cells, heart muscle cells, or brain cells. The resulting specialised cells are then available for a wide variety of potential uses, including the modelling and investigation of biological systems, toxicity screening for drugs, screening for regenerative drug development and transplanting the cells into humans to replace dead or diseased cells, for example in the case of a stroke or spinal cord injury. Cell culture experiments can also be useful in a wide range of other applications.

SUMMARY OF THE INVENTION

The invention is defined in the appended claims.

One embodiment of the invention provides a method of processing cell culture data. The data comprises results from a large number of samples, the results being obtained by performing multiple stages of cell culture in succession on each sample, where each stage represents a cell culture treatment having a particular set of conditions, such that each sample follows a protocol specified by the identity and order of the treatments applied to the cell culture. The method comprises specifying a subset of the samples that yielded a desired cell culture outcome; and performing a computer-implemented analysis of the results from the samples in the subset to produce an ordering or grouping of the results. The ordering or grouping helps to identify one or more protocols that are effective for obtaining the desired cell culture outcome, wherein the analysis for producing the ordering or grouping utilises information on similarities between different protocols.

The desired cell culture outcome may be specified by one or more conditions (which may potentially represent alternatives). The ordering or grouping of the results usually involves an ordering or grouping of the samples in the subset or an ordering or grouping of the protocols associated with the samples in the subset. In either case, the analysis seeks to identify protocols that generally have the best chance for being effective in obtaining the desired cell culture outcome and discriminating against samples that might represent false positives. This then allows better targeting of follow-up experiments, thereby reducing experimental time and cost.

In contrast with existing approaches (which treat different protocols as independent from one another), the analysis utilises information on similarities between different protocols. This then provides a mechanism for combining data from different protocols in order to achieve a more robust and accurate ordering/grouping (and hence a better identification of protocols for further investigation).

In one embodiment, the analysis for producing the ordering or grouping further utilises the number of samples from the subset that follow each protocol (in addition to information on similarities between different protocols). For example, if there are I protocols that gave at least one positive result, and I(n) is the number of samples that gave a positive result for the nth protocol, then we can define a score (S) for a given protocol (P(i)) as:

$$S(P(i)) = \sum_{k=1}^{k=I} I(k) \times WT(P(i), P(k))$$

where WT(P(i), P(k)) is a weighting factor based on the similarity between protocol P(i) and protocol P(k) (the higher the similarity, the higher the weighting factor). In this approach, a protocol scores more highly if it is more similar to other protocols that gave positive results (especially to other protocols for which multiple positive results were obtained). The ordering of the results can then be based on the score S for each protocol. It will be appreciated that this is just one possible formulation for the scoring, and the skilled person will be aware of many other possibilities.

The weighting factor in the above formulation can be considered as a form of distance measurement between the different protocols (where a high distance produces a low similarity, and hence a low weighting). One way of determining the weighting factor (or distance measurement) between the different protocols is to count the number of stages in common for the protocols concerned. For example, the weighting factor might be proportional to (or have any other suitable dependency on) the number of stages in common for the protocols concerned.

The above approach provides a binary measure (0 or 1) for comparing individual treatments (they are either the same or different). However, some embodiments may utilise a more graduated measure for comparing individual treatments. For example if treatment A involves using a first set of conditions and treatment B involves using a second set of conditions, then a similarity assessment may take into consideration how many conditions are in common between treatments A and B. Likewise, if treatments A, B and C all involve the same chemical but at different concentrations (A>B>C), then A might be regarded as more similar to B than it is to C (because it is closer in terms of concentration). Another possibilities is that treatments that activate similar pathways may be regarded as more similar than those that do not.

In one embodiment, the analysis is performed on a data set comprising a record for each sample in the subset. Each record may comprise an identifier of the sample and information on the protocol applied to the sample. The information on the protocol applied to the sample may comprise an ordered listing of the treatments applied to the sample. In other embodiments, the information in the records on the protocol may just comprise a label or other identifier of the protocol, which can then be used to access a separate data set that provides information (order and identity) for the treatments used in a given protocol.

In one embodiment, the ordered listing is represented as a binary string. Each bit in the binary string corresponds to a different treatment in a different stage, so for example, if there are 5 rounds, each with 8 possible treatments, then the string comprises 40 bits. The value of each bit in the binary string indicates whether or not a given treatment was applied to the sample for that particular stage. The use of a binary string in this manner makes it straightforward to count the number of common treatments between different protocols and provides a convenient form of input to various algorithms for grouping or ordering.

In one embodiment, the grouping or ordering comprises clustering the samples (or protocols). This clustering can be performed using various techniques, such as hierarchical clustering, a self-organising map, and so on. It will be appreciated that the region (or regions) of densest clustering (tightest grouping) tend to indicate protocols that are of most interest for further investigation, since these represent similar protocols that all yielded positive results. In contrast, low density of clustering (weak grouping) indicates protocols that yielded positive results, but where few (or no) other similar protocols yielded positive results. In general, the higher the density of a cluster, the lower the likelihood that the protocols involved in the cluster represent false positives.

Other techniques for analysing the results may produce an ordering rather than a clustering. For example, one approach is to give each sample (protocol) a score as described above, and the samples (protocols) can then be ordered or ranked in accordance with the score. In this approach, the samples (protocols) with higher scores tend to be more similar to other successful samples or protocols than samples (protocols) with lower scores. In general, the higher the score for a given sample (protocol), the lower the likelihood that it represents a false positive.

The results from the analysis (whether presented as a clustering, ordering, or any other suitable format) therefore help to identify the protocols that are of most interest, in that they have a relatively strong likelihood of producing the desired cell culture outcome. Accordingly, in one embodiment the method further includes using the grouping or ordering of the results to identify cell culture treatments for further investigation. The method may then comprise performing these further investigations into the identified cell culture treatments.

In one embodiment, the method may further comprise analysing the measurements of at least the subset of samples that yielded a desired cell culture outcome to determine the protocol for each sample in the subset. For example, different treatments may be arranged to impart different fluorescent tags to the samples, and the measurements may be performed by flow or scanning cytometry to identify the fluorescent tags associated with said samples. The results for a sample may be discarded if the measurements do not allow a reliable determination of the protocol for that sample, so that the results for the sample are not included in the grouping or ordering analysis. In some cases, a partial (rather than complete) protocol may be determined reliably. For example, the measurements may indicate clearly the treatment from one round, but not from another round. Such partial results may still be helpful, depending on the subsequent analysis to be performed.

In one embodiment, the desired cell culture outcome is determined by passing one or more tests. The method further comprises analysing the grouping of results to identify different groups of samples that pass said one or more tests. These different groups may represent different cell culture properties, for example, they may correspond to different cell phenotypes. Accordingly, the grouping is not restricted to identifying a single protocol or pathway of interest, but may also be used to identify different protocols that can lead to different outcomes (that fall within the general desired outcome). For example, a desired outcome might be cells of type A, but there may be subtypes of A1 and A2 that both correspond to type A. It has been found that two groupings of the results may correspond respectively to the two different subtypes, thereby demonstrating the biological significance of the groupings (for at least some data sets).

In one embodiment, the method comprises performing the multiple stages of cell culture to generate the results for processing. Hence some embodiments cover the complete procedure, from performing the original cell culture experiments, analysing the results, and then performing follow-up experiments based on the analysis of the results to confirm which protocols do indeed give the desired cell culture outcome.

One embodiment of the invention provides a computer program for implementing any of the methods described above. The computer program may be stored in any suitable computer readable medium, such as a flash memory, optical disk (e.g. CD, DVD), computer hard drive, etc. The computer program may be made available for download over a network such as the Internet.

Another embodiment of the invention provides an apparatus for processing cell culture data. The data comprises results from a large number of samples, the results being obtained by performing multiple stages of cell culture in succession on each sample, where each stage represents a cell culture treatment having a particular set of conditions, such that each sample follows a protocol specified by the identity and order of the treatments applied to the cell culture. The apparatus comprises a memory containing data specifying a subset of the samples that yielded a desired cell culture outcome; and a processor configured to perform a computer-implemented analysis of the results from the samples in the subset to produce an ordering or grouping for the results, said ordering or grouping helping to identify one or more protocols that are effective for obtaining the desired cell culture outcome, wherein the analysis for producing the ordering or grouping utilises information on similarities between different protocols.

The apparatus may be implemented by a computer system (or computer systems) programmed with suitable code. The code comprises program instructions for execution by one or more processors with the computer system. The code may be stored on a non-transitory medium, such as an optical disk, magnetic tape, and so on. Some implementations may use dedicated or special-purpose hardware for performing some or all of the processing or may be implemented using a suitably programmed general purpose computer workstation. The apparatus may be part of or integrated into a machine used in cell culture experiments. For example, the apparatus may comprise a flow cytometry system that is used both to generate the results from the cell culture experiments and also to then analyse the results by way of grouping or ordering. The apparatus may benefit from the same particular features as described above with regard to the method embodiment.

BRIEF DESCRIPTION OF THE DRAWINGS

Various embodiments of the invention will now be described in detail by way of example only with reference to the following drawings:

FIG. 5A illustrates in larger scale a portion of the diagram of FIG. 5.

DETAILED DESCRIPTION

Figure 1:
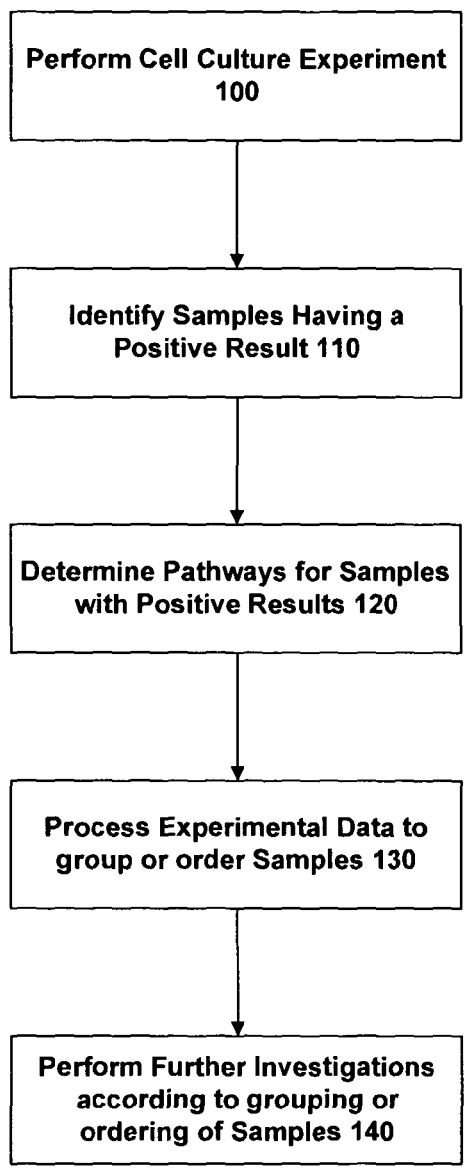
FIG. 1 is a high-level flowchart of a cell culture experiment and data processing in accordance with one embodiment of the invention.

FIG. 1 is a high-level flowchart of a cell culture experiment involving data processing in accordance with one embodiment of the invention. The flowchart commences with performing an in vitro cell culture experiment (operation 100) involving a large number of samples, for example many thousands of samples. Such a cell culture experiment is described, for example, in EP-A 1551954, in which each sample comprises a bead which acts as a substrate for the cell culture. Each sample is subjected to a series of treatments by immersing the bead into a succession of culture media. The sequence of treatments performed on any given sample can be considered as the protocol (pathway) for that sample.

The treatments are generally performed in stages or rounds, so that all the samples undergo the same number of rounds of treatment. Even if some samples receive a different number of treatments, the number of rounds of treatment can be homogenised across the sample set by "padding" the rounds for certain samples with null treatments as appropriate. This allows each sample to be considered as receiving the same fixed (predetermined) number of treatments.

If $N(i)$ is the number of different possible treatments in the ith stage or round, and there are I stages altogether, then the total number of protocols (N) for the experiment is given by $N=N(1) \times N(2) \ldots N(I)$. In general, the number of samples is chosen to be much larger than N, so that multiple samples (on average) will be exposed to each protocol.

As described in EP-A 1551954, there are many possible ways of dividing the samples for each round. One approach is to split the number of samples (e.g. beads) so that they are divided (approximately) evenly for each treatment in a round. The samples are then pooled together at the end of each round, before being split again for the next round. Providing the number of samples is significantly larger than the number of total protocols tested by the experiment, then this approach ensures on a statistical basis that multiple samples are exposed to each protocol.

Rather than pooling and then splitting at the end of each round, another approach is to split then pool. In other words, the samples from each treatment in the first round are split into the number of treatments in the second round. The portions or aliquots intended for each of the different treatments in the second round are then combined to commence the treatment. This approach provides a more precise distribution of samples across the protocols (rather than relying on a statistical distribution), but is more involved from an experimental perspective, since the amount of splitting and pooling is significantly greater.

Each treatment represents different physical, chemical and/or biological conditions for the cell culture. For example different treatments may involve different temperature or lighting conditions, the use of different growing media, the presence or absence of particular hormones, etc. The skilled person is well aware of the wide variety of different treatments that may be utilised, see EP-A 1551954 for further discussion.

The protocol for each sample is recorded for later detection and analysis. This recording may be done physically or chemically, for example by associating a particular fluorescent tag to every sample that undergoes a given treatment. The protocol followed by the sample can then be determined later from the set of tags associated with that sample. Another approach is to make each sample uniquely identifiable, for example by including an RFID tag in the sample. It is then possible to record the identity of each sample that receives a particular treatment, which in turn provides a record of the sequence of treatments received by any given sample. Further information about various ways to monitor and record sample protocols can be found in EP-A 1551954.

The results of the cell culture experiment are reviewed to determine those samples that have yielded positive results (operation 110). This may be achieved by flow cytometry or any other suitable technique. Note that a "positive" result here implies a desired outcome, which might be the presence (or absence) of a particular product or effect. The desired outcome may also represent a more complicated result, such as the presence of one substance and the absence of another substance. The positive samples can be considered as a subset of the original set of samples that were subjected to the cell culture experiments.

The experimental protocols for the positive samples are now determined (operation 120). This determination may be made by various techniques, see for example EP-A 1551954. Note that order of operations 110 and 120 is flexible. For example, in some experiment arrangements, the protocols may be determined for all samples. Once the subset of samples with positive results is identified, this leads directly to the subset of corresponding protocols. In other experiments, the samples with positive results may be determined first (as shown in FIG. 1). The treatment protocols are then identified only for this subset of positive samples (thereby reducing the number of protocols that need to be determined). In other experiments, the subset of positive samples may be identified simultaneously with the treatment protocols, for example by some suitable form of flow cytometry or scanning cytometry that can detect both the experimental outcome and protocol tagging at the same time.

We can label the treatments from the first round as 1A, 1B, 1C ... 1N, the treatments from the second round as 2A, 2B, 2C ... 2N, and so on. Note that:

(a) the number of different treatment options may vary from one round to another (i.e. "N" may vary between rounds);

(b) there may be any degree of overlap (zero, partial, complete) between the set of treatments from different rounds. For example, certain treatments from the first round might be the same as treatments from one or more later rounds (e.g. 1B=2C=3C). This can be helpful, inter alia, for investigating whether the time of exposure to a given treatment (or even the ordering of treatments) is significant.

(c) each round might possibly include a "null" treatment to reflect that one or more samples did not undergo any specific treatment in that round.

(d) not all possible protocols (i.e. potential combinations of treatments from the various rounds) are necessarily implemented. For example, if T1 and T2 are two treatments and it is desired to see if ordering is important, then we might set 1A=2A=T1 and 1B=2B=T2. In this case the sequences 1A-2B and 1B-2A are of interest, but simply repeating either treatment T1 or T2 (as for sequences 1A-2A and 1B-2B) may not be. Depending on the experimental protocol, the latter sequences might not be performed at all (particularly with a split-pool approach at the end of each round), although in other cases (e.g. with pool then split) it is easier to perform all protocols, given that those which do not produce positive results are not subjected to further analysis (as per operation 120).

The output of the experimental stage (and hence the input to the data processing stage of operation 130) is therefore a set of one or more successful protocols, where the success of each protocol is measured (for example) by a standard assay, and where each protocol is denoted by the series of treatments that form the protocol. For example, if there are four rounds of treatment, a protocol might be represented using the above nomenclature as 1C-2A-3C-4D. If multiple successful samples have followed the same protocol, then that protocol will be repeated multiple times in the data set.

The objective of large-scale cell culture experiments, and therefore of the data processing stage 130, is generally to identify protocols of particular interest. These protocols can then be subjected to further experimental investigation (operation 140), which can be a relatively expensive and time-consuming undertaking. Accordingly, it is important for the identification of protocols to be as effective as possible, especially in terms of ranking those protocols that are most likely to be worth pursuing, and also in terms of being able to discard false-positives (i.e. samples/protocols that have yielded spurious positive results).

Of the processing shown in FIG. 1, operations 100 and 140 are generally performed in a laboratory; operations 110 and 120 generally include a mixture of laboratory measurements and computer analysis; and operation 130 generally represents computer analysis. The laboratory measurements (and potentially the computer analysis as well) may be integrated into the cell culture experiment 100 itself, or may be performed subsequently in a separate investigation. The computer analysis may be performed using special purpose hardware, or using a conventional computer with memory, processor, etc, where the processor executes software that control the computer to perform the relevant actions.

In one implementation, the identification of pathways at operation 120 in FIG. 1 is performed by adding fluorescent tags to each pool for each round (split) of treatment. The tagging provides a unique identifier for each treatment across all rounds (rather than just within a round). However, no tags are used for the final round of treatments, since the particular treatment received by a given bead in the last round follows directly from the pool (vessel) which contains the bead at the end of the experiment. The fluorescent tags are generally significantly smaller than the samples, e.g. the beads (microcarriers), that are being used for the experiment, and adhere to the beads in a pool for a round of treatment. The number of tags that adhere to any given bead during any given treatment is variable, depending on experimental conditions, the particular properties of the bead, random fluctuations, etc. In some cases a given bead may pick up only a few (or possibly no) tags, while in other cases a given bead may pick up a hundred or more beads for a single treatment.

The tags may be identified by a combination of one or more properties, such as colour (of the fluorescence), size of the tag, and fluorescence intensity of the tag. In one particular implementation, there are three available sizes, denoted [3, 4, 5], there are two available colours, denoted [Red, Blue], and there are twelve available fluorescence intensities, denoted [01, 02, 03, 04, 05, 06, 07, 08, 09, 10, 11, 12]. The labelling of a given tag can then be represented, for example, as 4R11, which indicates a size of 4, colour Red, and intensity 11, or 3B03, which indicates a size of 3, colour Blue, and intensity 03. This gives a total of 3×2×12=72 unique identifiers.

TABLE 1

|  | T1 | T2 | T3 | T4 | T5 | T6 | T7 | T8 | T9 | T10 |
|---|---|---|---|---|---|---|---|---|---|---|
| Split 1 | 5R03 | 5R04 | 5R05 | 5R06 | 5R07 | 5R08 | 5R09 | 5R10 | 5R11 | 5R12 |
| Split 2 | 3R02 | 3R03 | 3R04 | 3R05 | 3R06 | 3R07 | 3R08 | 3R09 | 3R10 | 3R11 |
| Split 3 | 4R02 | 4R03 | 4R04 | 4R06 | 4R07 | 4R08 | 4R09 | 4R10 | 4R11 | 4R12 |

TABLE 2

|  | T1 | T2 | T3 | T4 | T5 | T6 | T7 | T8 | T9 | T10 | T11 | T12 | T13 | T14 | T15 |
|---|---|---|---|---|---|---|---|---|---|---|---|---|---|---|---|
| S1 | 4R02 | 4R03 | 4R04 | 4R06 | 4R07 | 4R08 | 4R09 | 4R10 | 4R11 | 4R12 | 3R07 | 3R08 | 3R09 | 3R10 | 3R11 |
| S2 | 5R03 | 5R04 | 5R05 | 5R06 | 5R07 | 5R08 | 5R09 | 5R10 | 5R11 | 5R12 | 3R02 | 3R03 | 3R04 | 3R05 | 3R06 |

Tables 1 and 2 illustrate the tagging scheme adopted in two different experiments, the first involving four rounds or splits, each of 10 different treatments (Table 1), the second involving three rounds or splits, each of 15 different treatments (Table 2). For each experiment there was no tagging in the final round (for the reasons explained above). Note also that the labelling of treatments as T1, T2 . . . T15 for each round does not indicate that the same set of treatments is used in all the rounds. Indeed, this will usually not be the case. In other words, although treatment T5 in split 1 may indicate the same as treatment T5 in split 2, most commonly it will denote a different treatment. Likewise treatment T5 in split 3 may represent another different treatment from T5 in split 1 and split 2.

In one embodiment, the tags associated with a given sample are separated from that sample for reading via flow (or scanning) cytometry. The flow cytometry produces four measurements for each tag: one representing the fluorescent wavelength, one represents the fluorescent intensity, and two denoting the scattering intensity for in the side and forward directions respectively. These four measurements enable the three parameters specified above (size, colour and intensity) to be determined, and hence the identity of the tag on a given bead or sample.

Figure 1A:
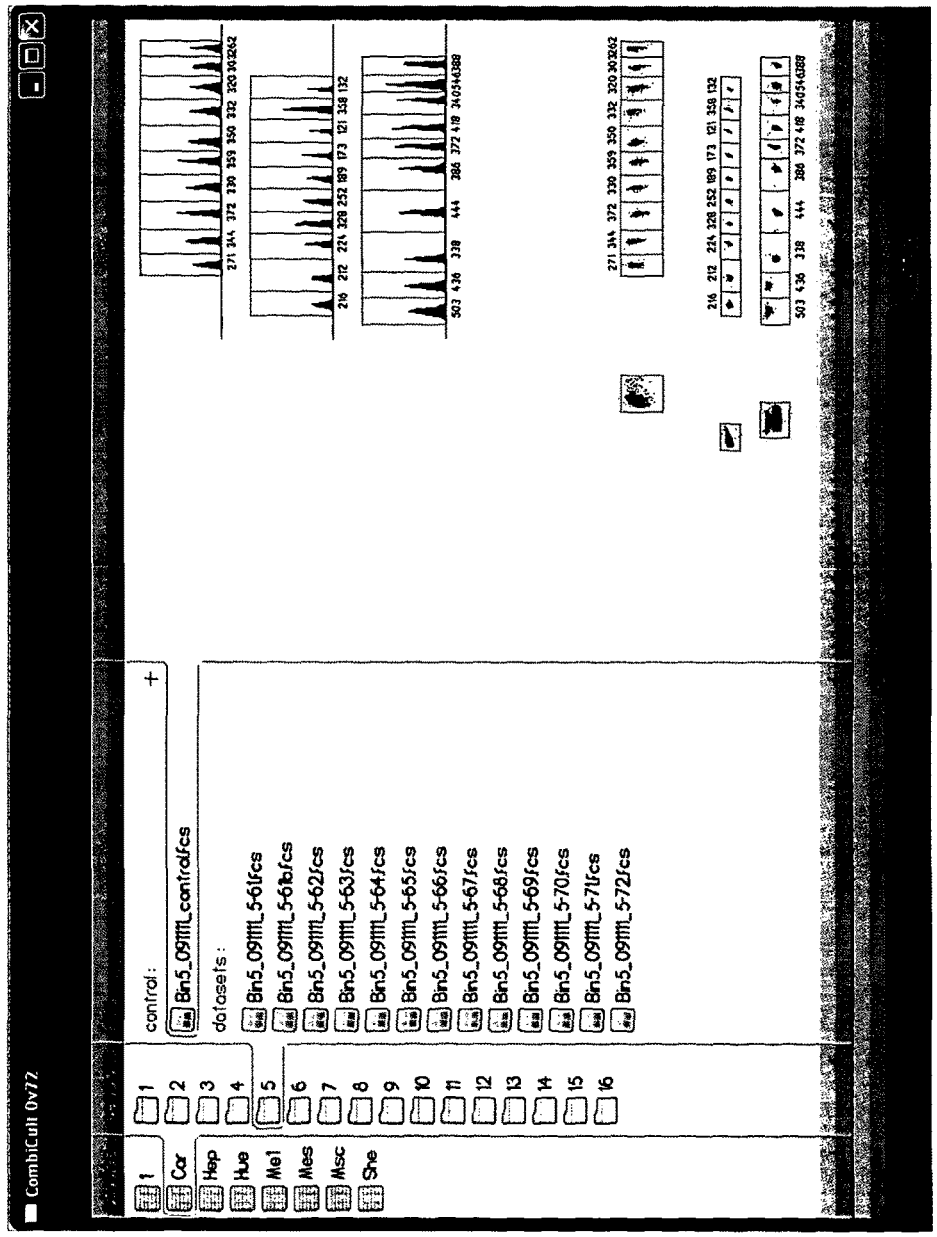
FIG. 1A is a screen shot of a calibration phase in analysis used for determining pathways in accordance with one embodiment of the invention for a first experiment.

FIG. 1A is a screen shot illustrating the computer-implemented calibration of the tagging for the experiment of Table 1 above. In this analysis system, the study column is used to select the results from a particular experiment. The session column is used to select a given session of flow cytometry measurements. Note that the different sessions of such measurements are calibrated separately, because the machine is subject to slight variations in output from one session to another.

The results for the tags obtained from each individual sample are contained in a set of files (one file for each sample), which are listed separately under the heading "datasets". In addition, there is a control file (as selected in FIG. 1A), which contains data obtained for tags that are measured at the start of the session. In one implementation, these tags for the control file are the same as the tags used in the cell culture experiment, but do not represent tags that have actually gone through the experiment itself attached to samples. In other implementations, the calibration could be performed directly using tags removed from samples that have gone through the experiment. Note that in this latter case, the calibration may use tags from samples irrespective of whether or not the samples have yielded a positive result (since this will give more data points for the calibration).

The right-hand portion of the screen in FIG. 1A contains three plots. The bottom-left plot has the X-axis representing side scattering and the Y-axis forward scattering. The three different sizes of tags can be clearly seen by the clusters separated out along the Y-axis, which are delineated by three separate boxes. The cluster with the lowest Y-axis value corresponds to size 3, the cluster with the middle Y-axis value corresponds to size 4, and the cluster with the largest Y-axis value corresponds to size 5.

The bottom-right plot on the right-hand portion of the screen in FIG. 1A extends the data in each of the three boxes from the left-hand portion along a Z-axis, which represents intensity values at a red fluorescent wavelength—since the experiment of Table 1 used tags all of the same colour, no plots along a fourth axis (intensity values at a blue fluorescent wavelength) are displayed. It can be seen that each of the three clusters (boxes) in the bottom-left plot comprises multiple clusters in the bottom-right plot, each cluster corresponding to different intensity. These different intensities are again delineated by separate boxes. The number associated with each box shows the number of tags falling into that box.

The top-right plot shows three rows of boxes corresponding to the three rows of boxes in the bottom-right (each row corresponding to one of the boxes in the bottom-left plot). The boxes in the top-right plot are histograms showing the distribution of the number of tags according to Z-value within each box from the bottom-right plot.

In one embodiment, the analysis of a data set for a flow cytometry session involves first plotting the data from a control file into a scatter diagram (such as shown bottom-left). The clusters of data (i.e. the three clusters shown bottom-left in FIG. 1A) are then demarcated by boxes (either by a user by hand, or by computer analysis). Within each box shown bottom-left, a corresponding ladder is determined for the corresponding clusters shown bottom-right (again either by a user by hand, or by computer analysis). Each segment of a ladder corresponds to a different tag intensity (for that size of tag).

Figure 1B:
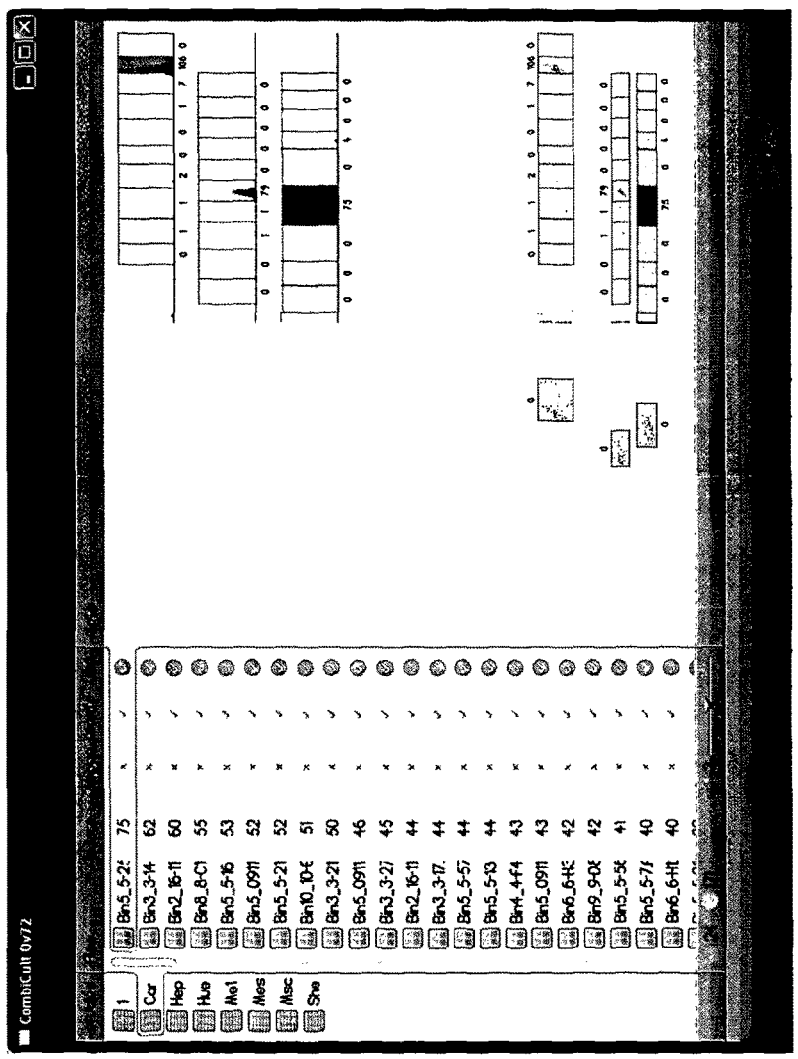
FIG. 1B is a screen shot of determining a pathway for one sample in accordance with one embodiment of the invention for a first experiment.

FIG. 1B shows the tag in a similar configuration to FIG. 1A, except that the data all comes from a single sample. In this case the boxes/ladder positions are maintained from the analysis of the overall data set in FIG. 2A (rather than being recalculated). It can be seen that on average, the sample has picked up (very approximately) 100 tags for each treatment, and there is a clear clustering of the tag measurements within each box. Thus for size 3 the tags are predominantly clustered in the fifth segment of the ladder, which corresponds to tag 3R06 from Table 1. For size 4 the tags are likewise predominantly clustered in the fifth segment of the ladder, which corresponds to tag 4R07 from Table 1. For size 5 the tags are predominantly clustered in the ninth segment of the ladder, which corresponds to tag 5R11 from Table 1.

Figure 1C:
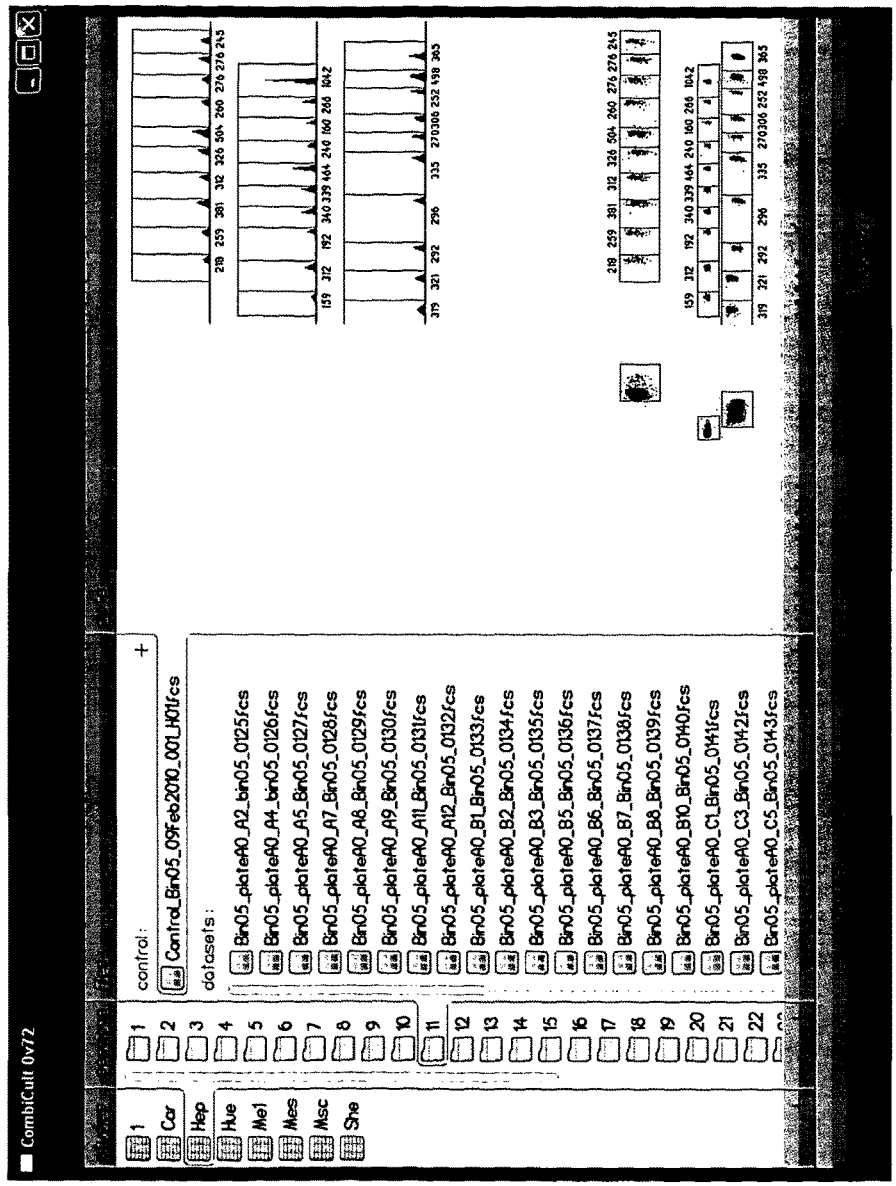
FIG. 1C is a screen shot of a calibration phase in analysis used for determining pathways in accordance with one embodiment of the invention for a second experiment.
Figure 1D:
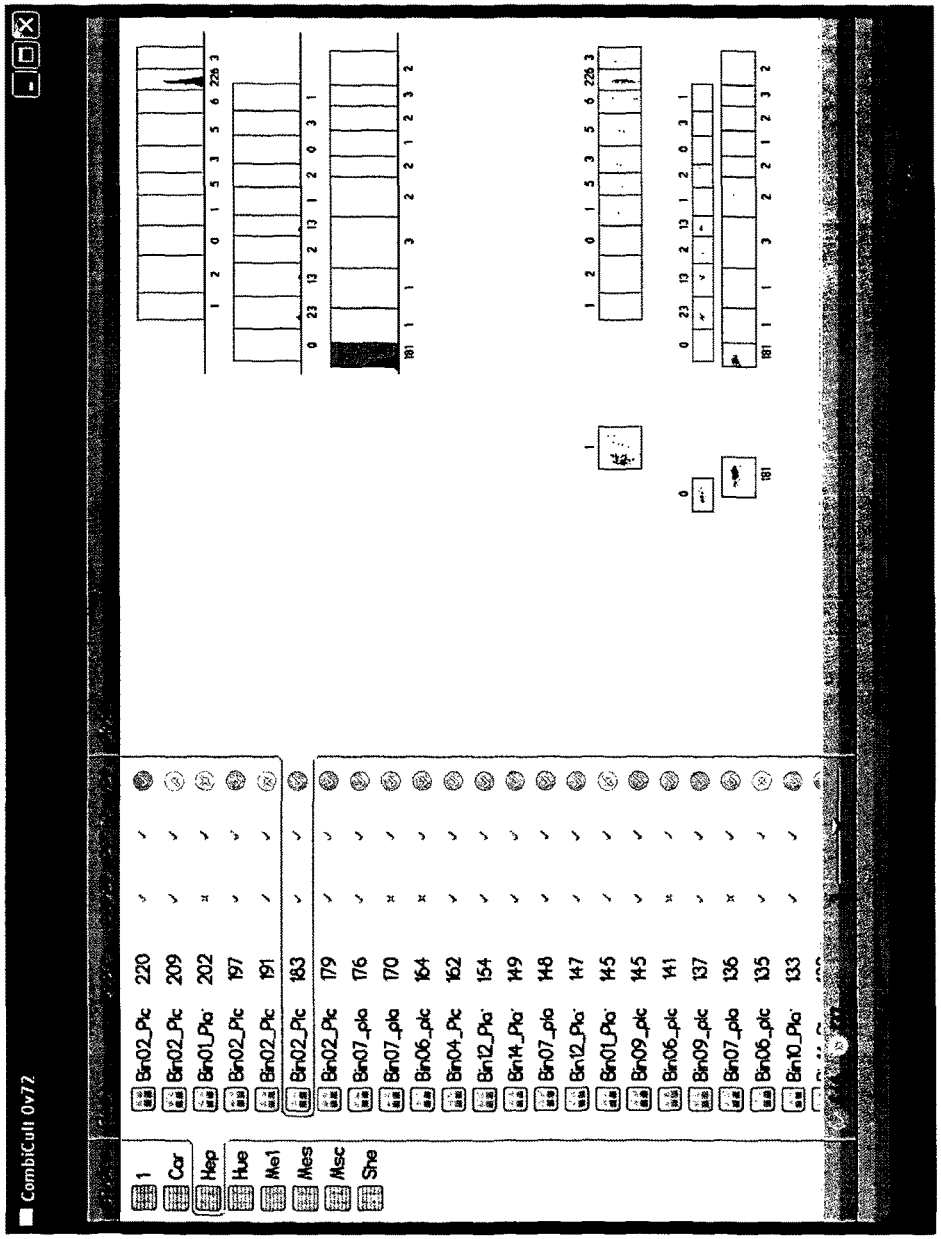
FIG. 1D is a screen shot of determining a pathway for one sample in accordance with one embodiment of the invention for a second experiment.

FIGS. 1C and 1D are generally similar to FIGS. 1A and 1B respectively, but correspond to the experiment of Table 2 rather than Table 1. Thus FIG. 1C depicts the results from the complete set of samples in the control file, while FIG. 1D depicts the results from just a single sample. It is clear that the sample of FIG. 1D followed the treatments corresponding to the lowest intensity size 4 tag used (4R02) and the second largest intensity size 5 tag used (5R11).

Although the plots of FIGS. 1B and 1D clearly identify the relevant pathways of the samples concerned, in some cases the tag measurements do not always support an unambiguous identification. This may arise for various reasons, such as a sample not picking up enough tags in a given treatment or possibly losing the tags in a subsequent treatment (or during later processing). In addition, if first and second samples are in the same split for a later round of treatment, the first sample might be contaminated by tags transferred from a second sample (where the transferred tags correspond to a treatment in an earlier round that was undergone by the second sample but not by the first sample). A further possibility is that there are problems in performing the optical measurements on the tags.

Moreover, even if the tags for a particular sample can be reliably assigned to one or more treatments, this assignment must correspond to an available pathway. In particular, the tag identification must lead to one treatment for each split. If no treatments are identified within a particular split for a sample, this leads to an incomplete identification of the pathway for the sample. On the other hand, if multiple treatments are identified within a single split for a sample, this indicates some error (for example, two beads having stuck together during a particular treatment), and no complete pathway can be determined for the sample. In this instance partial pathways may be determined, for example knowledge of the treatments in the last and second to last split.

Accordingly, operation 120 in FIG. 1 (determining pathways) may involve discarding or rejecting samples for which the pathway cannot be reliably determined (even if such samples have yielded a positive result). It will be appreciated that a variety of statistical tests can be used for deciding on the reliability of a given pathway. The overall number of positive samples (with reliable pathways) produced by a given experiment may therefore vary somewhat according to the particular statistical test and associated threshold that are adopted for accepting/rejecting determinations of pathways (and whether or not partial pathways, as mentioned above, are being utilised).

As discussed above, one approach for analysing data from large-scale cell culture experiments is to count the number of successful samples (cell units) that have followed a particular protocol. The protocols are in effect ranked according to how many samples have followed that particular protocol. Note that in this approach, each protocol is treated independently of the other protocols in determining a statistic (the number of samples associated with that protocol) that is then used for ranking/selecting protocols for further investigation. In contrast, the approach described herein for processing the cell culture experimental data (as per operation 130) looks for dependencies or relationships between protocols, such as grouping or ordering the protocols based on a measurement of distance between the various protocols. This approach has been found to provide increased insight into the potential value of the protocols concerned.

Figure 2:
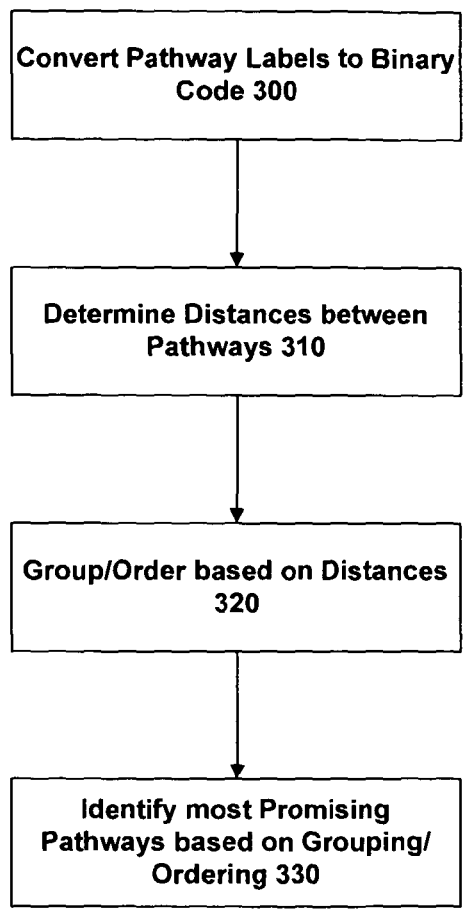
FIG. 2 is a high-level flowchart of processing data from a cell culture experiment in accordance with one embodiment of the invention.

FIG. 2 is a high-level flowchart illustrating the processing of the data analysis operation 130 of FIG. 1 in accordance with one embodiment of the invention. The processing begins with converting the identified protocol (pathway) labels into a binary representation (operation 300). In particular, if there are 6 possible treatments (say) in the first round, then this round is represented by a binary string of six bits containing one bit equal to 1, and the remaining bits equal to zero. The location of the "1" in the bit string indicates the corresponding treatment. For example, we could have 1A=100000, 1B=010000, 1C=001000, 1D=000100, 1E=000010, and 1F=000001. The treatments for subsequent rounds can likewise be represented by binary strings. The overall treatment can then be indicated by concatenating together the binary strings for the different rounds, or by forming a vector, where the number of elements in the vector corresponds to the number of rounds, and each element comprises the binary string for the associated round.

The processing now determines the similarity (distance) between protocols (operation 310). This can be done in various ways. One approach (for example) for any two protocols is to (a) perform, for each round of treatment, an AND operation on the two binary codes corresponding to that round, and (b) sum the number of non-zero results from (a) across all the rounds of treatment. The result of this processing represents the number of rounds of treatment in common (overlap) between the two protocols. This overlap may be zero (no rounds in common), partial (some but not all rounds in common), or complete (all rounds in common) and can be considered as a form of distance measurement between the two protocols.

Another way of looking at this is to consider the binary codes for a given round as locating the various protocols in an N-dimensional space (where N is the number of treatment options in the round). The distance values in this space between treatments for a given round are then quantised to zero (if coincident) and one (if non-coincident).

The processing now performs a grouping or ordering based on the determined distance or similarity measurements (operation 320). Contrary to existing approaches, which perform ordering/ranking based on a single figure for each protocol (the number of samples that followed this protocol), where this single figure is determined independently of all other protocols, the approach of FIG. 2 involves dependencies between protocols. In particular, the distance measurements are calculated for different pairs of protocols, and these distance measurements are then used to determine the grouping or ordering.

There are various known algorithms for grouping or ordering the protocols using the distance measurements. These include hierarchical clustering, self-organised mapping and fingerprint analysis. These algorithms look at relatedness, e.g. some form of distance or similarity, between protocols to perform a grouping, ordering, or other organisation of the samples/protocols. The use of this relatedness between protocols provides an extra dimension of information to be extracted from the cell culture experimental results, and accordingly results in a more powerful analysis of the results. This in turn allows a more sensitive and effective discrimination (at operation 330) of those protocols that should be investigated further (as per operation 140 in FIG. 1).

The skilled person will appreciate that the various operations shown in FIG. 2 may be modified according to the particular implementation. For example, the conversion of protocol labels to binary code at operation 300 provides a mapping into a multi-dimensional space which can then be used to determine the distances between protocols at operation 310. However, the similarities or distances for use in the grouping/ordering might be obtained via some other mechanism (without reference to location in a multi-dimensional space). One possibility is that a pair of treatment labels such as 1B and 1D might be used to access a distance figure from a lookup table, where this distance would then feed through into the grouping/ordering. In these circumstances, the conversion to binary of operation 300 would not be required. Another possibility is that each pathway is represented by a unique label which links to a table containing information on the treatments associated with that pathway. The pathway labels could then be used to extract the corresponding pathway information from the table for performing the similarity/distance calculations as appropriate.

In some embodiments, the binary codes for the various protocol treatments are fed directly into the grouping/ordering algorithm, without first explicitly calculating any distances (i.e. omitting operation 310 as a separate step). In this approach, the distances or some corresponding measure of relatedness are implicitly determined as part of the grouping/ordering algorithm. The skilled person will be aware of further potential modifications to the processing shown in FIG. 2.

An example of the data analysis operation 130 of FIGS. 1 and 2 will be now be described in conjunction with data from an experiment illustrated in FIG. 3. This experiment involved 300,000 samples (biopolymer beads) and commenced with pluripotent stem cells. Each sample was subjected to four rounds of treatment, with each round comprising ten possible different treatments. The samples were pooled and then re-split (randomly and evenly) after each of the first, second and third rounds of treatment. Consequently the experiment involved 10,000 ($10^4$) possible protocols, so that 30 beads should have followed each protocol (on average).

After the fourth (final) round of treatment, the beads were scanned for two different positive outcomes: (a) the presence of phagocytes (which ingest marked E. coli cells)—, and (b) the presence of green fluorescent neural cells. The experiment yielded 101 beads (samples) with positive results for (a), and 84 beads with positive results for (b) (for which the complete protocol for each bead (sample) was accurately determined). The data processing of the results for the phagocytes will now be described in detail.

The data set from the cell culture experiments was formatted into an ASCII file, with a separate record for each bead. Each record comprised a tab-separated list of bead identifier and forty associated binary descriptors (corresponding to the binary coding discussed above). This data set was then subjected to cluster analysis to classify the beads into groups based on similarity. As described above, the samples can be considered as locations or vectors within an N-dimensional space, where N is equal to the number of descriptors per sample (here 40, for the ten different treatments in each of four rounds). Similarities can then be calculated based on Euclidean distance or any other appropriate measurement (which may be symmetrical or asymmetrical, depending on the particular application).

Figure 4:
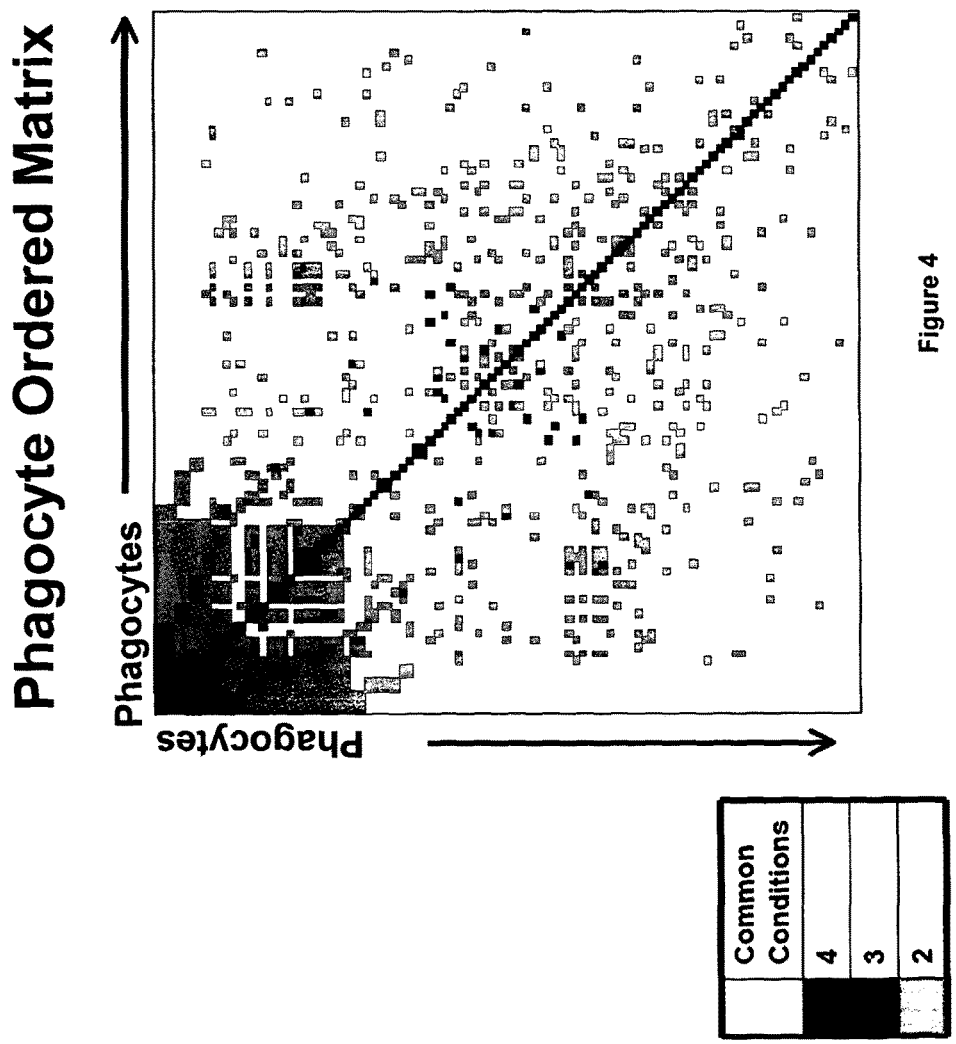
FIG. 4 is a diagram showing ordered data from the experiment of FIG. 3.
Figure 4A:
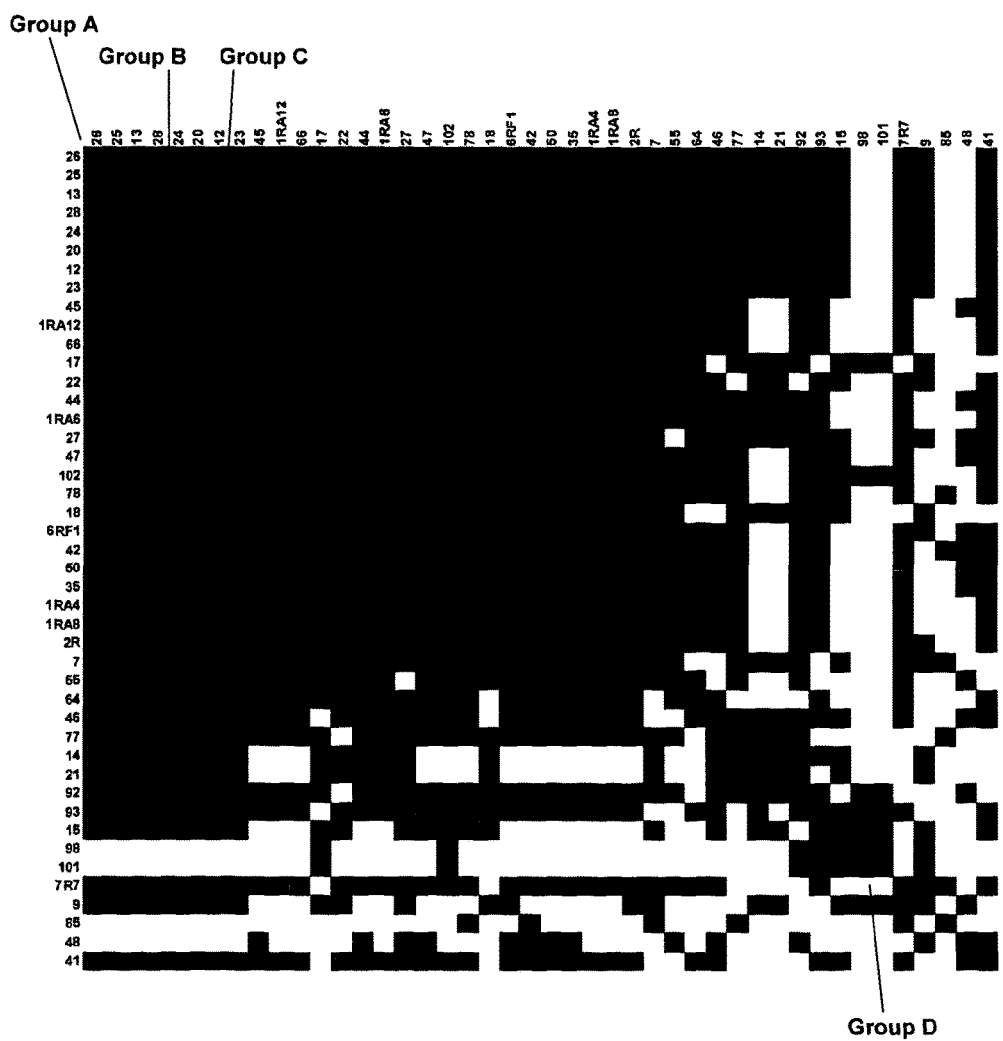
FIG. 4A is a diagram showing in more detail a region of FIG. 4.

FIG. 4 is a plot of some results from the above experiment (with FIG. 4A illustrating the top left corner of FIG. 4 in more detail). The x and y axes represent an ordered listing of each sample/bead that produced a positive result for the presence of phagocytes (with the same ordering on each axis). Each square of the plot depicts the number of stages in common for the pair of beads concerned. In particular, a black square indicates four stages in common, a dark square indicates 3 stages in common, a middle-toned square represents 2 stages in common, a light square represents one stage in common, and a white square indicates zero stages in common. The identities of the beads are labelled in FIG. 4A along the x and y axes. These labels allow each bead to be uniquely identified. (The rationale behind the precise labelling scheme used in FIG. 4A is not relevant to an understanding of the present invention). It will be appreciated that the diagonal from top left to bottom right is black because this represents the intersection of each bead with itself (so necessarily there are four stages in common). The plot is also symmetric about this diagonal because determining the number of stages in common is a commutative operation.

The beads are ordered on the axes as follows. Each bead can be considered as having a vector (N4, N3, N2, N1, N0), where N4 is the number of other beads that the bead shares all four stages with, N3 is the number of other beads that the bead shares 3 stages with, N2 is the number of other beads that the bead shares 2 stages with, etc. Assuming that there are T beads in total (which are successful), then N4+N3+N2+N1+N0=T (including for each bead the match with itself in the value for N4). Any two beads are then ordered with respect to one another in accordance with their value of N4. If they have the same value of N4, then they are ordered with respect to one another in accordance with their value of N3. If they have the same value of both N4 and N3, then they are ordered with respect to one another in accordance with their value of N2, and so on.

In this approach, beads with a high affinity (relatedness or similarity) to other beads are generally gathered top left in the plot. As discussed above, the number of stages in common between beads can be considered as a measure of the similarity (distance) between the beads (or more accurately, between the corresponding experimental protocols). It will be appreciated that this is an inverse relationship, so that a high number of stages in common (high similarity) represents a low distance between beads, while a low number of stages in common (low similarity) represents a high distance between beads. Note that FIG. 4A only depicts a subset of the successful beads (some of the beads with low affinity to the other beads are omitted).

As discussed above, a common conventional approach for identifying protocols of interest is to look for situations where multiple successful beads have followed the same protocol. According to the data of FIG. 4, there are four successful protocols which were followed by two or more beads. These are specifically indicated in FIG. 4A as Group A (beads 26, 25 and 13), Group B (beads 28 and 24), Group C (beads 20 and 12), and Group D (beads 98 and 101).

In a conventional counting approach, Group A might be considered as the most promising group because it contains most beads (3), but it would then be difficult to distinguish between the remaining 3 groups, each of which contains 2 beads. The plot of FIG. 4A however reveals a significant difference between Groups A, B and C on the one hand and Group D on the other hand. The relatively dark shading in the top left corner of the FIG. 4A illustrates that Groups A, B and C are all clustered together, with significant mutual overlap. This makes it very likely that a good protocol for producing the desired end result can be found in or close to the protocols involved in these groups.

In contrast, the black square of Group D is relatively isolated, with very little overlap (relatedness) with the other successful beads, and particularly with respect to Groups A, B and C. This can be seen clearly from FIG. 4A by the (substantially) white rows and columns in which the small black square for Group D is located. This might indicate that the protocol of Group D is very sensitive to particular conditions, which could in itself make the protocol relatively unattractive (since it might be difficult to perform on a reliable basis). Another possibility is that Group D is just a chance occurrence, and does not actually represent a valid protocol. We can estimate the likelihood of such a chance occurrence by assuming that 100 successful beads are distributed randomly across the 10000 possible protocols, and calculating the probability that a given protocol is shared in such circumstances by two or more beads. This is given by $1-(9999!/9900!*10000^{99})\approx 39$, so that in fact, a spurious grouping in the positive results is not very unlikely.

It will be appreciated that a probability calculation (either theoretical or by simulation) can be used to assess the statistical significance of any given result. For example, the probability of getting at least a triplet (three samples all sharing the same protocol) on a purely random basis is given by:

$$1 - \frac{\sum_{d=0}^{I/2} \binom{N}{d}\binom{N-d}{I-2d}\frac{I!}{(2!)^d}}{N^I}$$

where N is the total number of possible pathways, I is the number of positive results, and the count over d reflects the number of doublets (two samples both sharing the same protocol) (so if I is odd, then the count terminates at (I−1)/2). This information can then be used to (i) help recognise potential false-positives, and (ii) design the initial experimental parameters, such as the number of beads, etc., in order to enhance statistical reliability.

For example, for N=10,000 and I=101 (as for the data set of FIG. 4) the possibility of obtaining a triplet as a chance occurrence is found from the above equation to be about 0.0016. Therefore, while a doublet (two positive samples sharing the same protocol) might well be a chance occurrence (as indicated by the probability of 0.39 determined above), this is much more unlikely in the context of a triplet.

The ordering of the samples in FIGS. 4 and 4A does not clearly segregate Group D from Groups A-C, even though the plot strongly suggests that they are unrelated. This segregation may be made clearer with other ways of ordering the samples on the axes. For example, one possible way would be to give each bead a score, where the score is obtained by adding up the total number of stages in common for that bead with the other beads. For example, if there are 101 beads, a particular bead shares four stages in common with two beads (including itself), three stages in common with 6 beads, two stages in common with 11 beads, one stage in common with 23 beads, and no stages in common with the remaining beads, this could give a score of (2×4)+(6×3)+(11×2)+(23×1)=71. The score therefore reflects some form of overall (average or aggregate) distance of a given bead from all the other beads. The beads can then be ordered along the axis in accordance with this score. This approach would result in a much higher score for groups A, B and C than for group D, hence groups A, B and C would remain clustered together, while group D would be separated. It will be appreciated that this is just one illustrative technique for ordering based on distance, and the skilled person will be aware of many other possible methods for performing such ordering.

Figure 3:
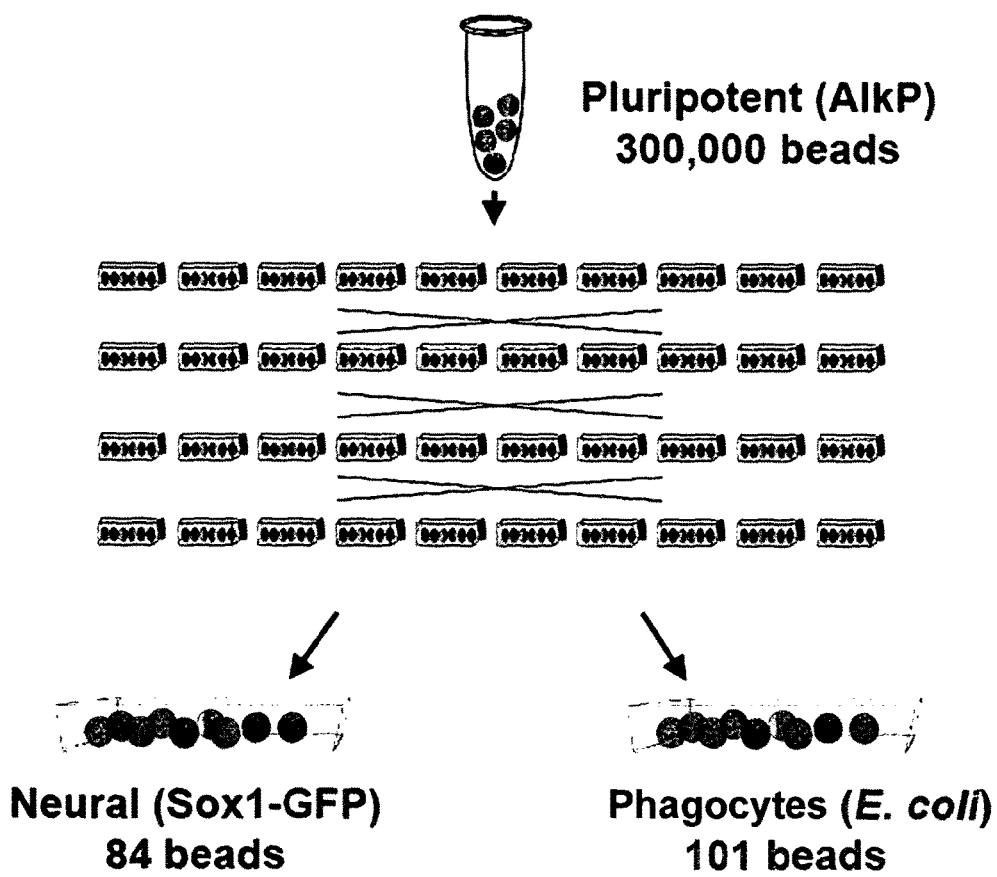
FIG. 3 is a schematic diagram of one cell culture experiment which generated a set of results for data processing in accordance with one embodiment of the invention.
Figure 5:
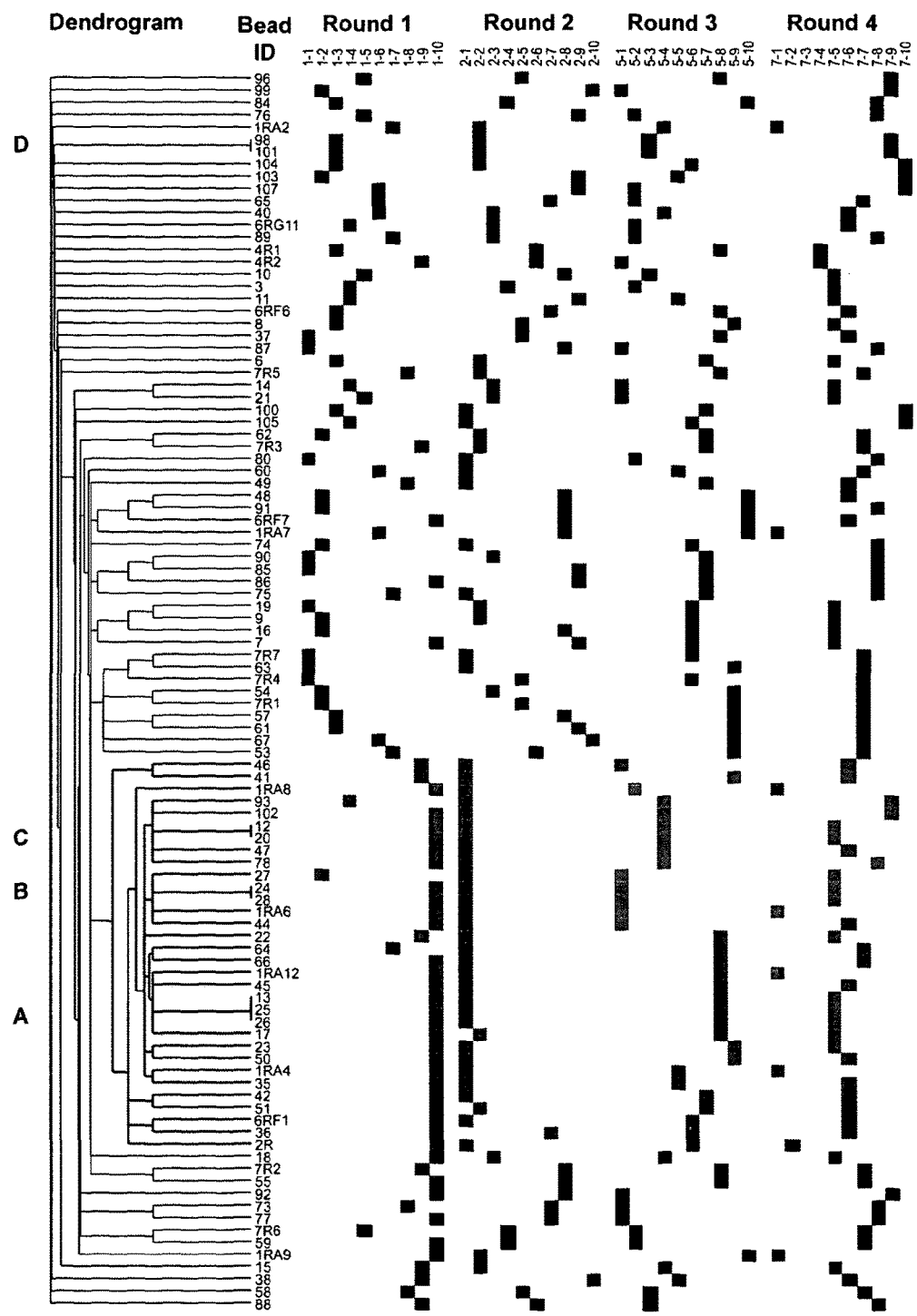
FIG. 5 is a diagram showing data from the experiment of FIG. 3 grouped using hierarchical clustering.

FIG. 5 illustrates a different mechanism for processing the results from the cell culture experiment of FIG. 3 (rather than the plot of FIG. 4), namely hierarchical clustering. Each row in FIG. 5 corresponds to a successful bead, as indicated in the column headed Bead ID. Note that the labels applied to the beads in FIG. 5 are the same as the labels shown in FIG. 4 (which enables the results of these two different grouping mechanisms to be compared directly with one another).

FIG. 5 also depicts four column blocks, each column block representing one round of treatments, as indicated by the column block headers. Each column block is subdivided into ten columns, each column representing one treatment for that particular round. Each row (bead) has one dark square in each column block, indicating the treatment received by that bead for that particular round.

The left-hand side of FIG. 5 shows a dendogram, which illustrates the hierarchical clustering of the beads (and which determines the order in which the beads are listed). The dendrogram can be considered as a form of family tree, in that it shows which beads are closest to other beads in terms of the distance (relatedness) between their respective protocols. The further left that you have to go in the dendrogram, i.e. the higher up the hierarchy, to link two beads, the further apart those beads are considered to be.

The hierarchical clustering of FIG. 5 was performed using the program Cluster 3.0, and the dendogram is depicted using the Java Treeview program. The Cluster program is described in "Cluster Analysis and Display of Genome-Wide Expression Patterns" by M Eisen et al, Proceedings of the National Academy of Science, USA, 1998, 95 14863.

Hierarchical clustering can be agglomerative (bottom-up) or divisive (top-down). According to the former approach, all objects or samples initially represent their own, individual cluster, and these are then aggregated together. In one agglomerative algorithm, the pair separated by the shortest inter-point distance forms the first cluster. The next cluster is again formed between the two objects with the shortest inter-point distance, where an object can represent either an individual sample, or a previously created cluster. This procedure then continues until a tree is created that spans the whole dataset.

The hierarchical clustering algorithm includes a mechanism to determine an inter-point distance when one or more of the objects is a cluster (rather than an individual sample). The mechanism for doing this is usually termed linkage, and can be based on various criteria, such as the mean difference between cluster members, the maximum (or minimum) distance between cluster members, etc. The selection of linkage method, as well as choice of the distance or similarity metric and also the initial ordering of the input data, may impact the output of the clustering analysis.

FIG. 5 shows four groups where more than one bead shares a given protocol. These groups are the same as shown in FIG. 4 (and are indicated by the same lettering). It is readily apparent from the dendogram that Group D is separate from Groups A, B and C, the same conclusion as was apparent from FIG. 4. As previously discussed, there is a strong suggestion from this configuration that Group D represents a spurious positive (despite two beads sharing the same protocol).

One way of describing the degree of clustering in FIG. 5 is to use the nomenclature "aCb", where "a" is a number of beads, and "b" is the number of protocol stages in common.

Using this nomenclature, Group A can be denoted as 3C4 (3 beads sharing all four stages in common), while Groups B, C and D can all be denoted as 2C4 (2 beads sharing all four stages).

FIG. 5A is an enlarged view of the portion of FIG. 5 that contains the Groups A, B and C. Looking at the treatments in the four column blocks, it is readily apparent that most of the variability in terms of treatment between the beads in this section occurs in the third and fourth rounds. In contrast, a significant proportion of beads in this cluster use treatment 1-10 in the first round and treatment 2-1 in the second round, strongly suggesting that these treatments make an important contribution towards obtaining a positive result.

Figure 6A:
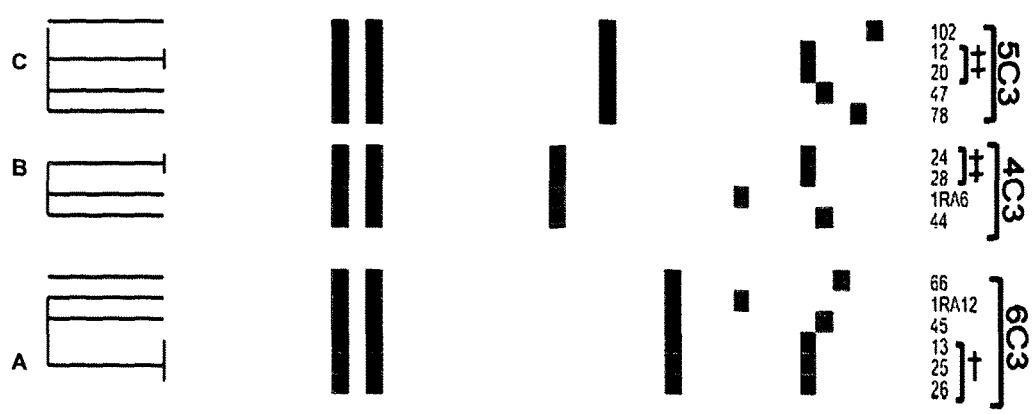
FIG. 6A illustrates in larger scale one clustering arrangement of data from the diagram of FIG. 5.

FIG. 6A shows three clusters from the data of FIG. 5A, omitting certain beads that lie between the clusters. The locations of Groups A, B and C from FIG. 5 are also shown in FIG. 6A. The clusters of FIG. 6A are denoted as 5C3, 4C3 and 6C3, indicating that they involve 5 beads, 4 beads and 6 beads respectively that share three treatments in common. In all three cases, the only variation in treatment occurs in the final round of treatment.

Figure 6B:
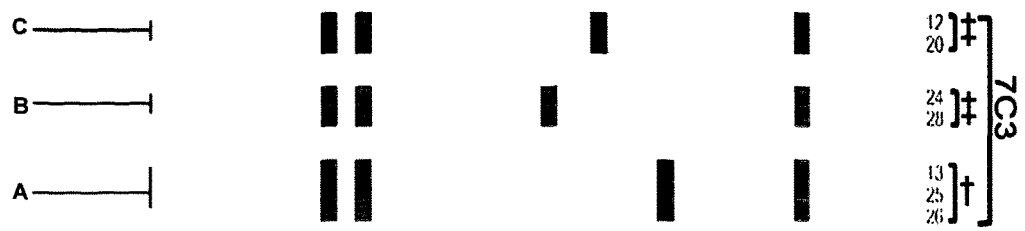
FIG. 6B illustrates in larger scale another clustering arrangement of data from the diagram of FIG. 5.

FIG. 6B shows another cluster from the data of FIG. 5A. This cluster comprises the seven beads of Groups A, B and C, and is formed by omitting certain intervening beads from the ordering shown in FIGS. 5 and 5A. The cluster of FIG. 6B can be described as 7C3, namely seven beads sharing three treatments in common. Note that for these seven beads, the variation occurs in the third round of treatment (rather than the fourth round of treatment as in FIG. 6A).

FIGS. 6A and 6B illustrate that there are various possible ways to view the clustering of the experimental data set from FIG. 3, for example, at different levels of the cluster hierarchy. In this context, the configurations of FIG. 6A and FIG. 6B can be regarded as complementary presentations of the same underlying data set, highlighting different aspects of the relationships between beads/protocols. This combination of viewpoints can then lead to an enhanced overall understanding of the data set for selecting which protocols to investigate further.

The ordered plot of FIG. 4 and the dendograms of FIGS. 5 and 5A can likewise being considered as complementary presentations of the same data, since they both reflect the same underlying property (relatedness), although they measure slightly different aspects of this property. This is further demonstrated by the fact that the highest ranked samples from FIG. 4 also correspond to the samples at the lowest level in the dendogram of FIG. 5A (i.e. the most tightly clustered). This provides additional confirmation of the importance of this small subset of samples.

The results of FIGS. 4-6 were generated by representing each treatment within a round by a binary digit to indicate whether or not that treatment was performed for that round. For example, if there are four possible treatments, A, B, C and D, these could be represented by (1000), (0100), (0010) and (0001) respectively. However, other embodiments may utilise a different, more detailed, representation of the various treatments. For example, each treatment may involve certain conditions selected from an overall set of conditions X1, X2, X3, Y1, Y2, Z1 and Z2. If A involves (X1, X2, Y2) and B involves (X1, X2, Y1, Z1), then we might label these two treatments as (1100100) and (1101010) respectively by assigning a binary digit to each possible condition within the treatment. These labels specify the conditions for a treatment could then be used as input to the clustering algorithm (or other form of ordering or grouping for the samples).

Figure 7:
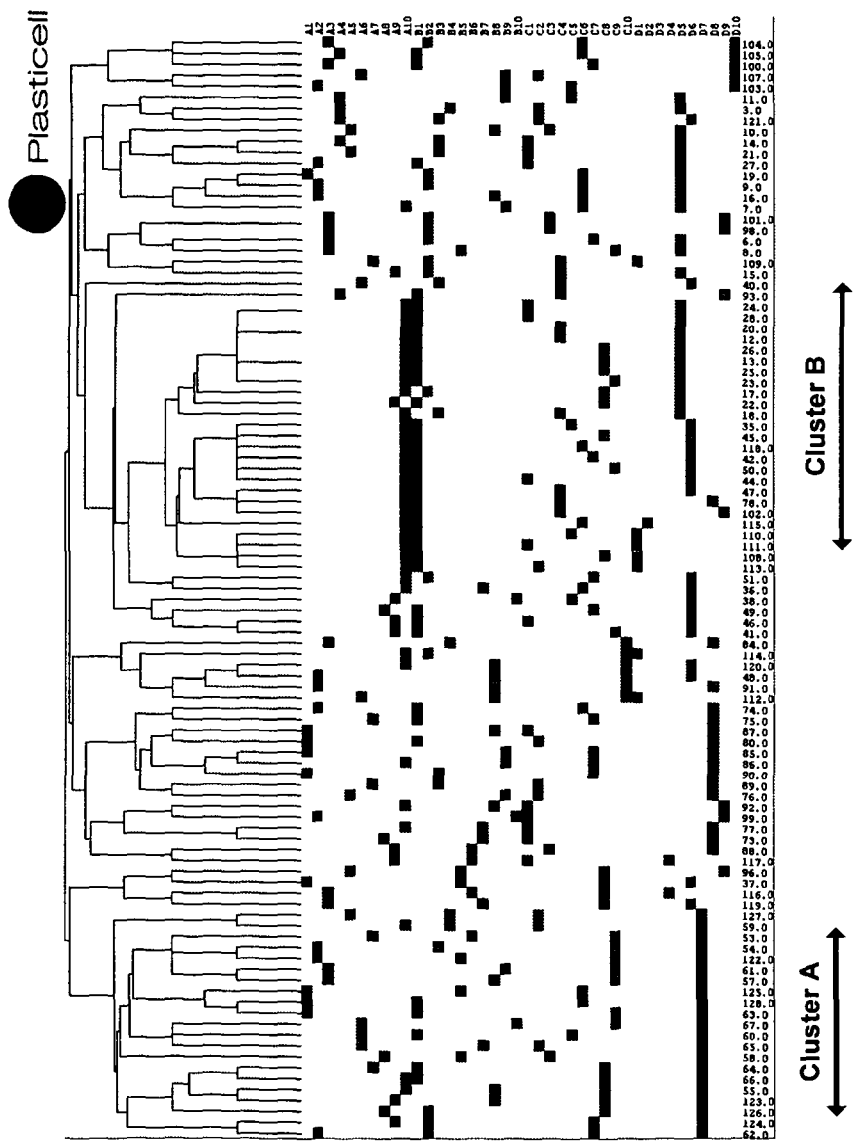
FIG. 7 is a diagram showing data from the experiment of FIG. 3 grouped using hierarchical clustering (as a variation on the clustering of FIG. 5)

FIG. 7 illustrates the results of hierarchical clustering performed using the Cluster 3.0 software on the same data set as for FIGS. 4-6. The configuration of FIG. 7 is similar to FIG. 5, in that each row corresponds to a particular round/treatment (as indicated on the right-hand side), while each end-point in the tree (cluster) diagram corresponds to a positive bead. (Bead identifiers are listed across the bottom of FIG. 7, but the identifiers used are somewhat different from those used in FIG. 5). The clustering results of FIG. 7 are similar (but not identical) to the clustering shown in FIG. 5. This variation can be attributed to differences in the way the clustering was performed, such as a different ordering of the input data, a different definition for determining a distance to a cluster, and so on.

FIG. 7 depicts two distinct clusters. The first cluster, denoted as Cluster A in FIG. 7, corresponds to pathways AX-BX-C8/C9-D7. The second cluster, denoted as Cluster B in FIG. 7, corresponds to pathways A10-B1-CX-D1/D5/D6. Note that in this nomenclature, Cluster B represents treatment 10 in split A, treatment 1 in split B, any treatment in split C, and treatment 1, 5 or 6 in split D. Note also that cluster B corresponds generally to the cluster shown in FIG. 6B, but with some additional samples for other treatments in split D.

The biological screen used to identify samples having a positive result in this experiment (corresponding to operation 110 in FIG. 1) was an E-coli internalization assay for phagocytosis. Since a number of cell phenotypes display phagocytosis properties, this screen is not specific to a single phenotype. Phenotyping the differentiated cells produced when the pathways corresponding to clusters A and B above were further investigated has demonstrated that the two clusters differentiate cells into different phenotypes.

Figure 8A:
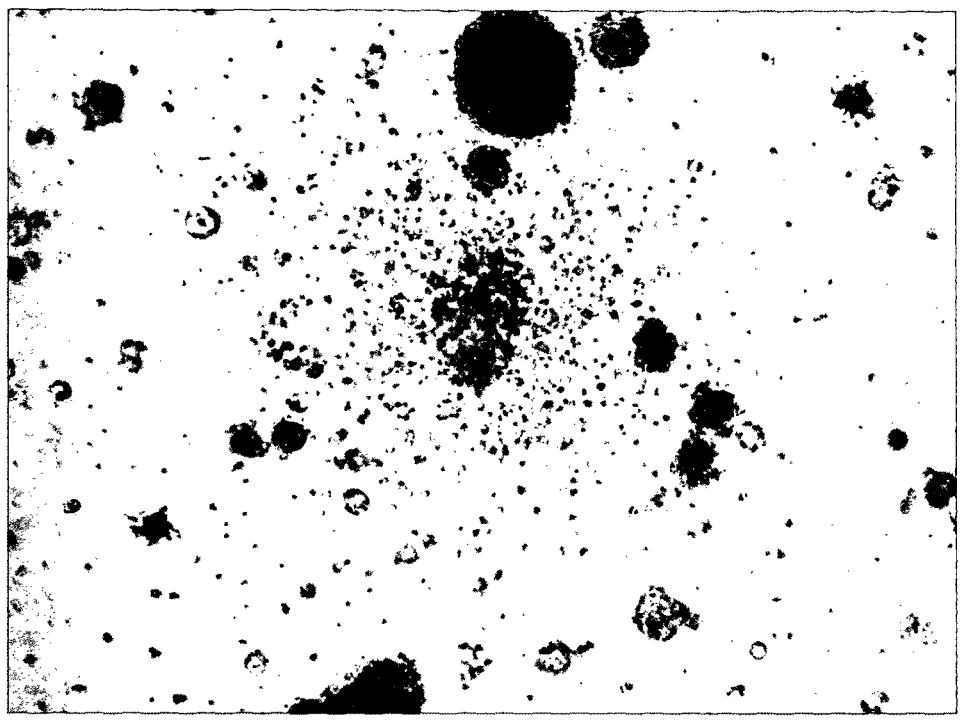
FIG. 8 corresponds to pathway 10-8-8-7 and shows granulocyte type cell colonies (FIG. 8A) and monocytic type cell colonies (FIG. 8B).
Figure 8B:
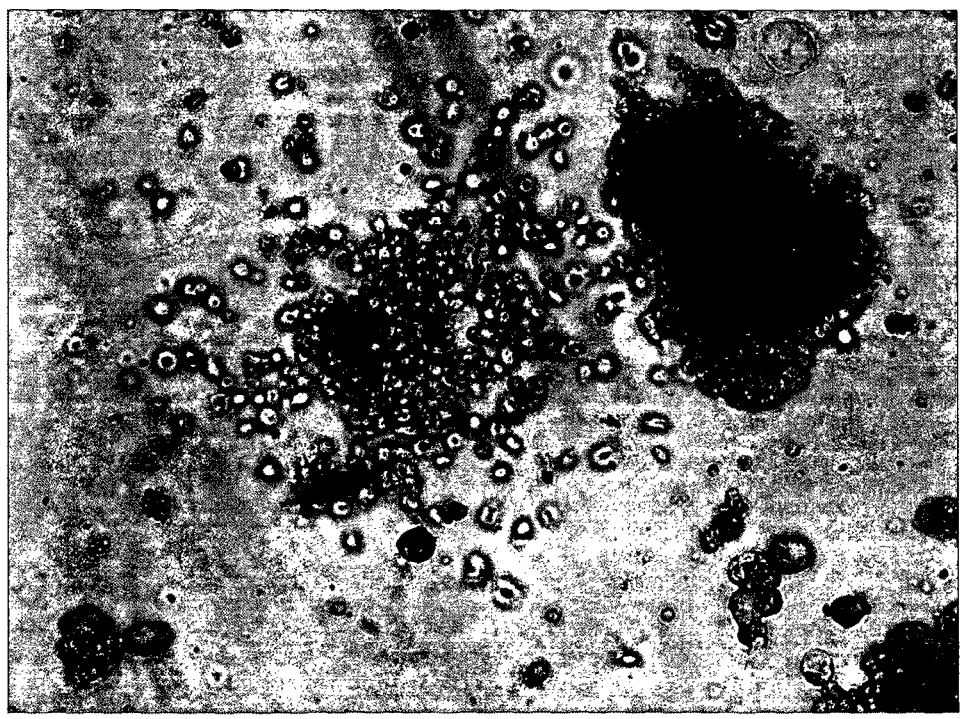
Figure 9A:
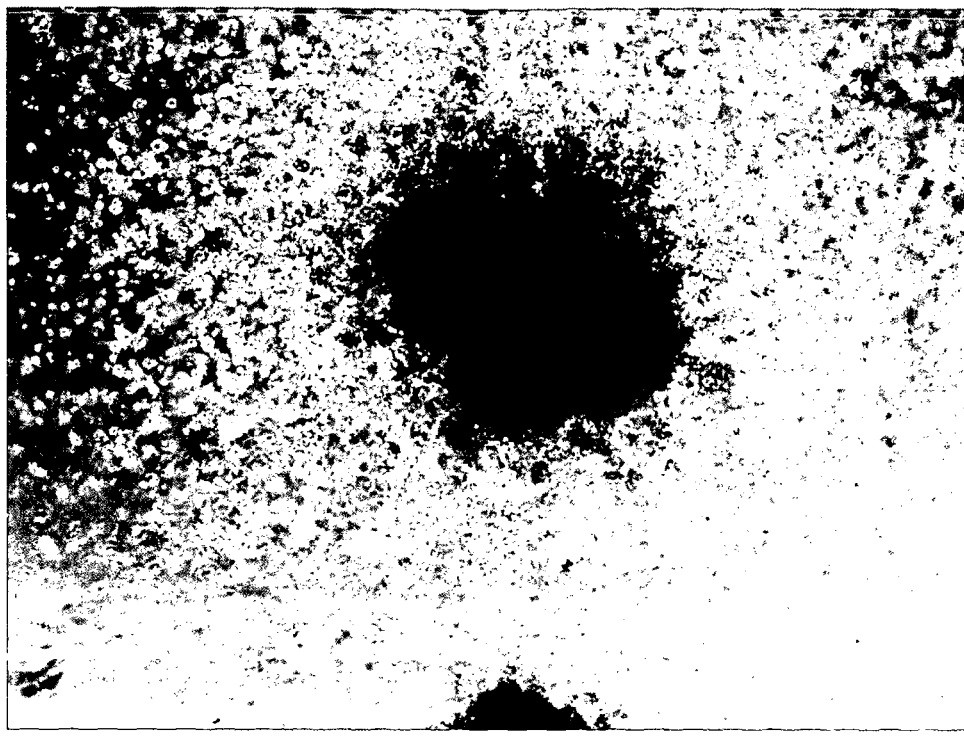
FIG. 9 corresponds to a bead that followed pathway 3-8-9-7 and shows granulocyte type cell colonies (FIG. 9A) and granulocyte, erytrocytic, monocytic and megakaryocyte (GEMM) mixed type cell colonies (FIG. 9B).
Figure 9B:
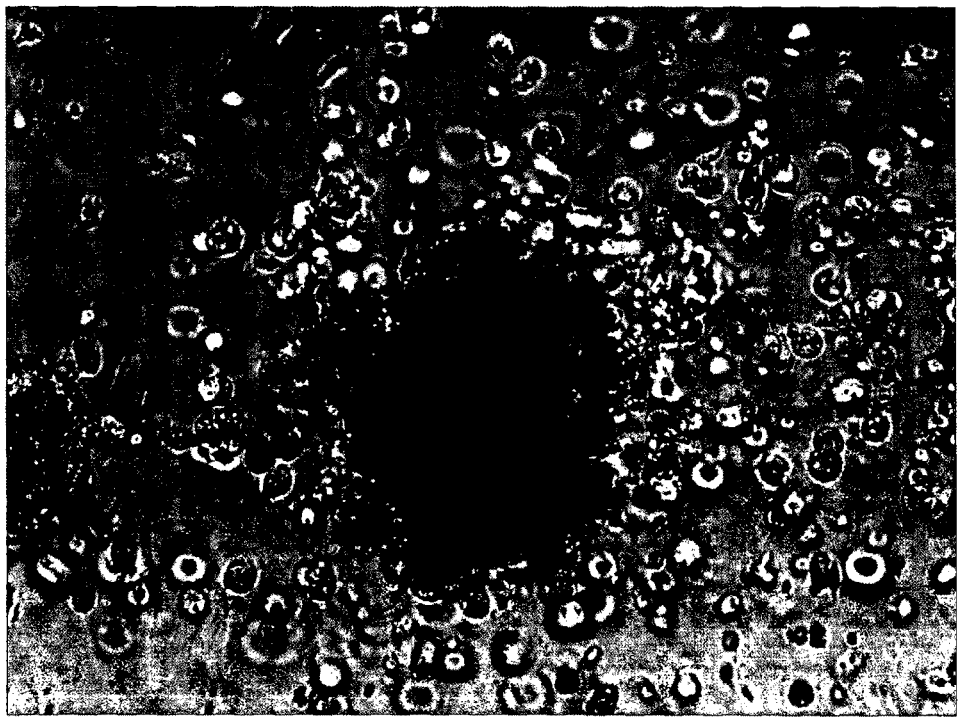
Figure 10A:
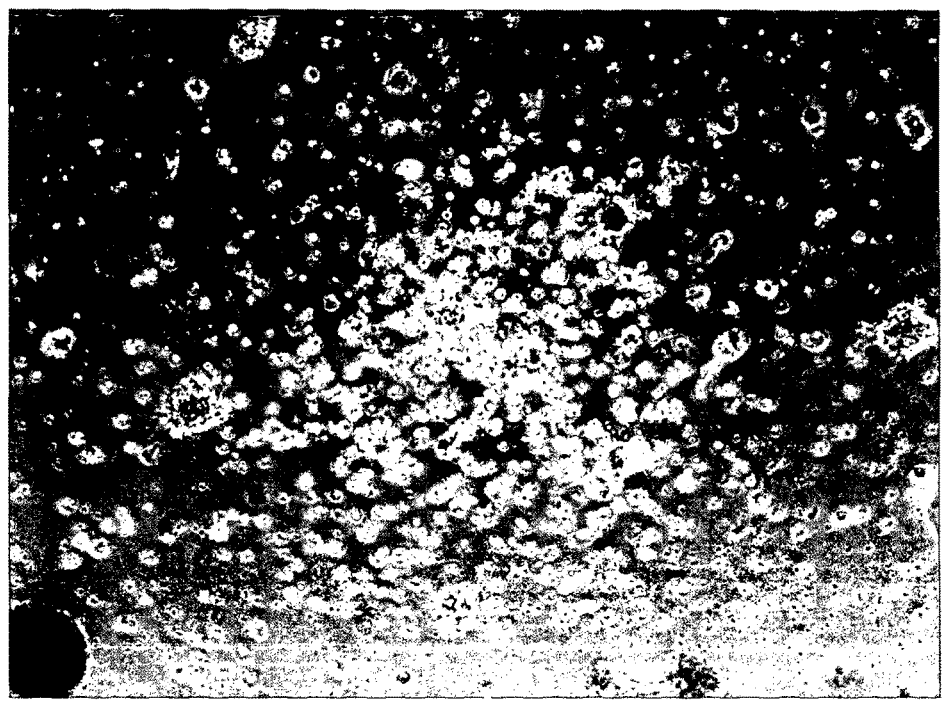
FIG. 10 corresponds to a bead that followed pathway 2-2-7-7 and shows granulocyte type cell colonies (FIG. 10A) and monocytic type cell colonies (FIG. 10B).
Figure 10B:
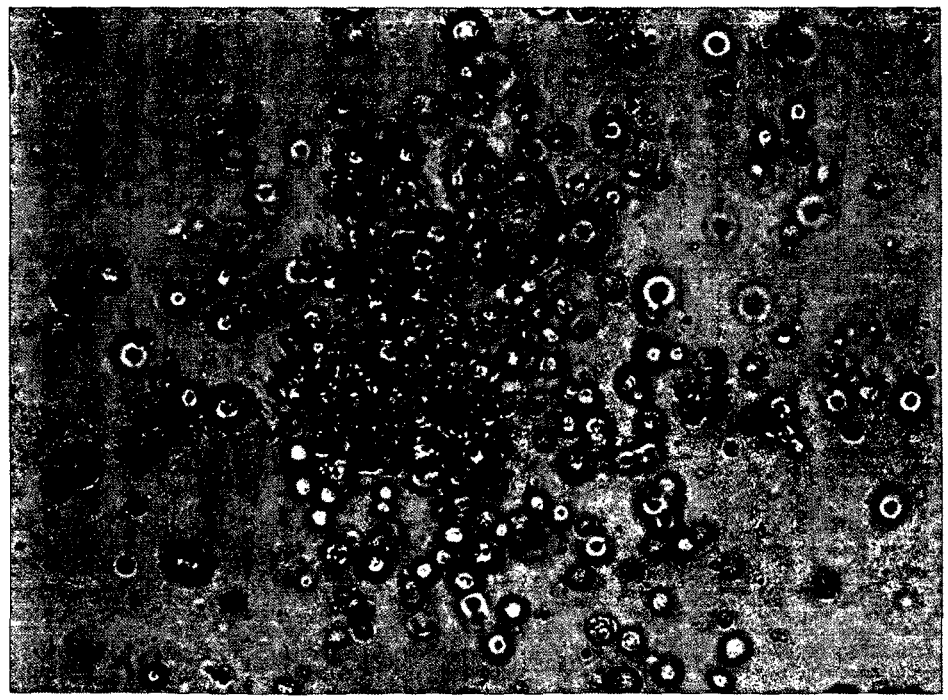

For cluster A, pathways from this cluster were found to generate hematopoietic precursors by day 9. These precursors gave rise to monocytic, granulocytic and erytrocytic colonies in colony formation assays in semi-solid medium, as illustrated in FIGS. 8, 9 and 10. In particular, FIG. 8 corresponds to a bead that followed pathway 10-8-8-7 and shows granulocyte type cell colonies (FIG. 8A) and monocytic type cell colonies (FIG. 8B). FIG. 9 corresponds to a bead that followed pathway 3-8-9-7 and shows granulocyte type cell colonies (FIG. 9A) and granulocyte, erytrocytic, monocytic and megakaryocyte (GEMM) mixed type cell colonies (FIG. 9B). FIG. 10 corresponds to a bead that followed pathway 2-2-7-7 and shows granulocyte type cell colonies (FIG. 10A) and monocytic type cell colonies (FIG. 10B).

Figure 11A:
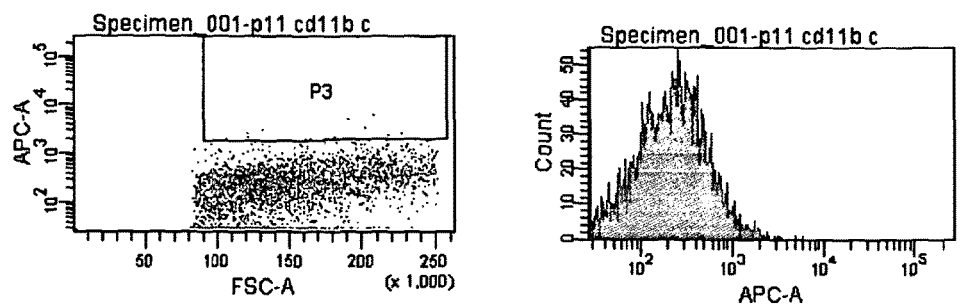
FIG. 11 depicts flow cytometry analysis of cd11b stained cells with FIG. 11A depicting an isotype control and FIG. 11B corresponding to pathway 2-2-7-7.
Figure 11B:
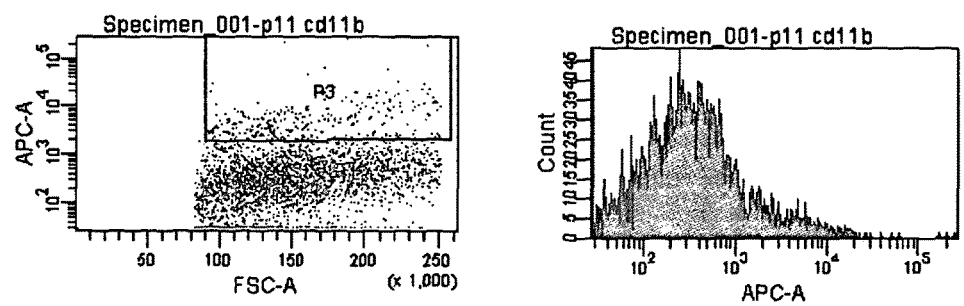

Cells produced by pathways included in cluster A were isolated from semi-solid media and stained positively for pan-leucocyte marker cd45 and myleoid lineage marker cd11b as shown in FIGS. 11-15. In particular, these Figures show:

FIG. 11—flow cytometry analysis of cd11b stained cells with FIG. 11A depicting an isotype control (0.3% of population positive) and FIG. 11B corresponding to pathway 2-2-7-7 (9.7% of population positive).

Figure 12A:
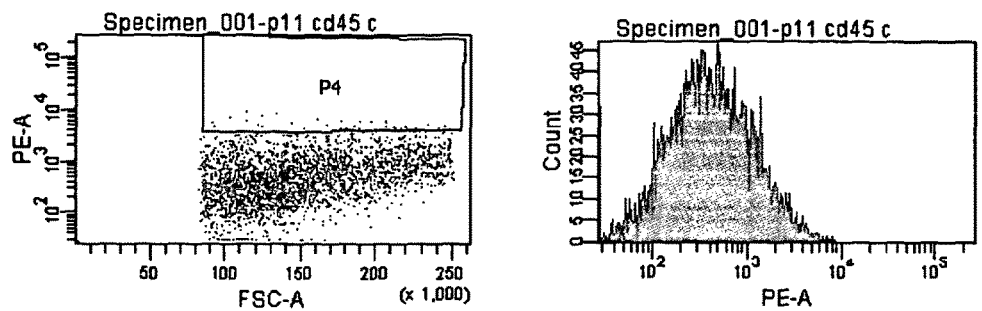
FIG. 12 depicts flow cytometry analysis of cd45 stained cells with FIG. 12A depicting an isotype control and FIG. 12B corresponding to pathway 2-2-7-7.
Figure 12B:
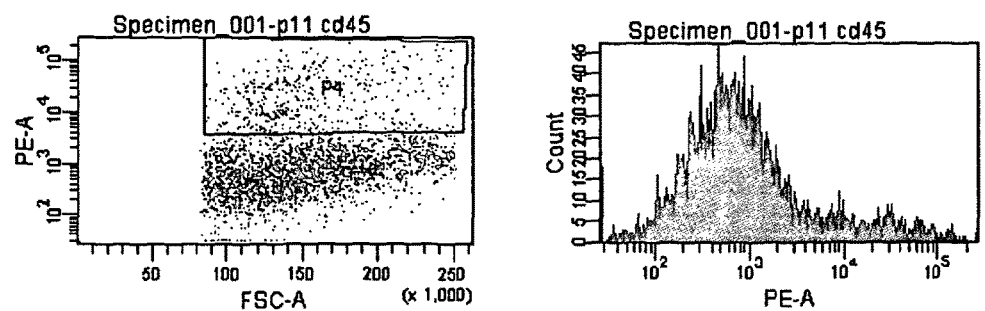

FIG. 12—flow cytometry analysis of CD45 stained cells with FIG. 12A depicting an isotype control (0.9% of population positive) and FIG. 12B corresponding to pathway 2-2-7-7 (15.6% of population positive).

Figure 13A:
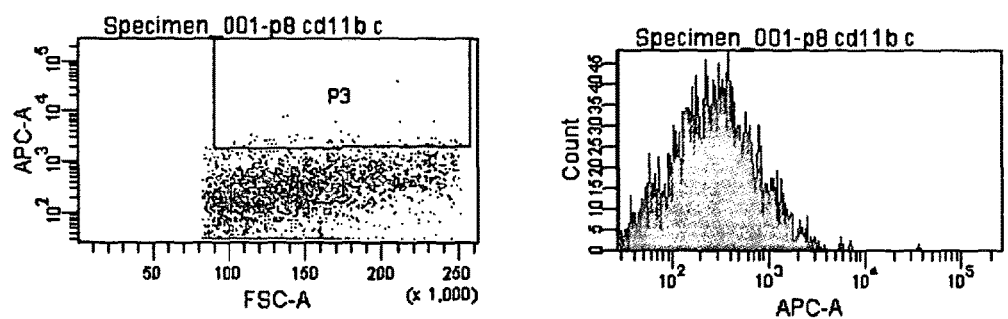
FIG. 13 depicts flow cytometry analysis of cd11b stained cells with FIG. 13A depicting an isotype control and FIG. 13B corresponding to pathway 10-8-8-7.
Figure 13B:
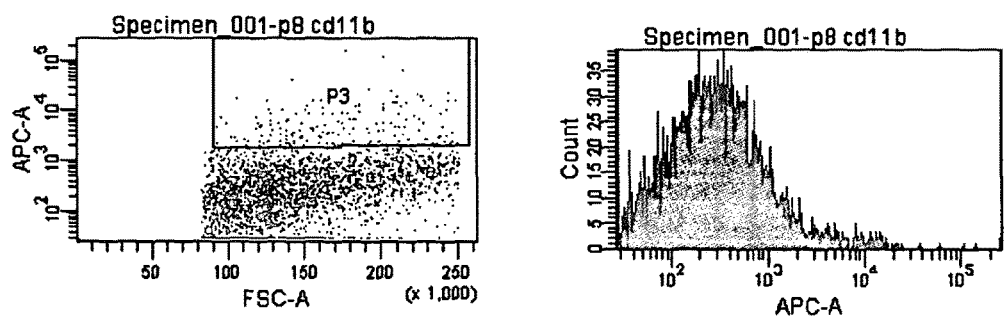

FIG. 13—flow cytometry analysis of cd11b stained cells with FIG. 13A depicting an isotype control (1.8% of population positive) and FIG. 13B corresponding to pathway 10-8-8-7 (5.5% of population positive).

Figure 14A:
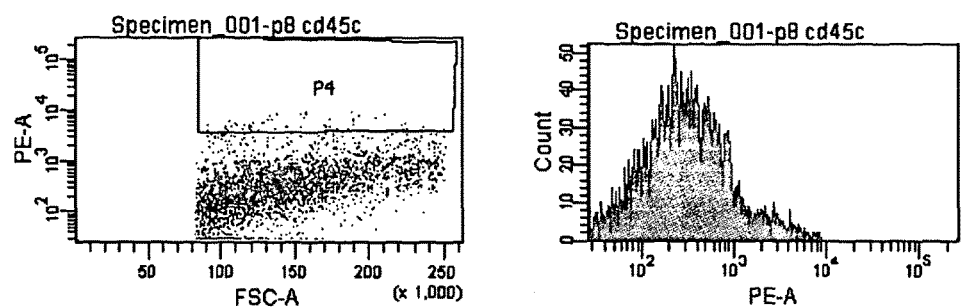
FIG. 14 depicts flow cytometry analysis of CD45 stained cells with FIG. 14A depicting an isotype control and FIG. 12B corresponding to pathway 10-8-8-7.
Figure 14B:
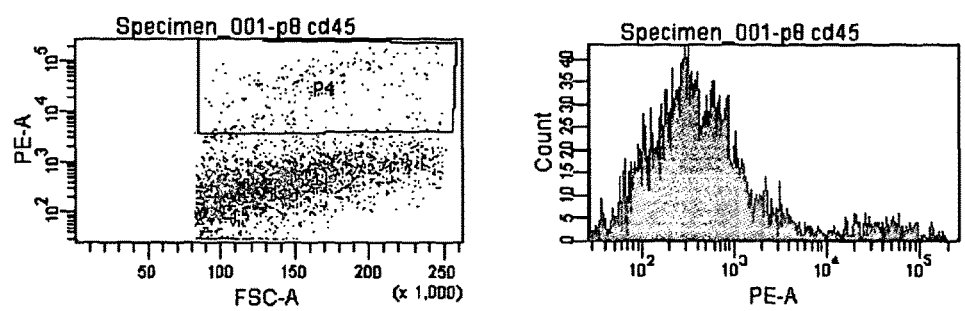

FIG. 14—flow cytometry analysis of CD45 stained cells with FIG. 14A depicting an isotype control (1.7% of population positive) and FIG. 12B corresponding to pathway 10-8-8-7 (8.7% of population positive).

Figure 15A:
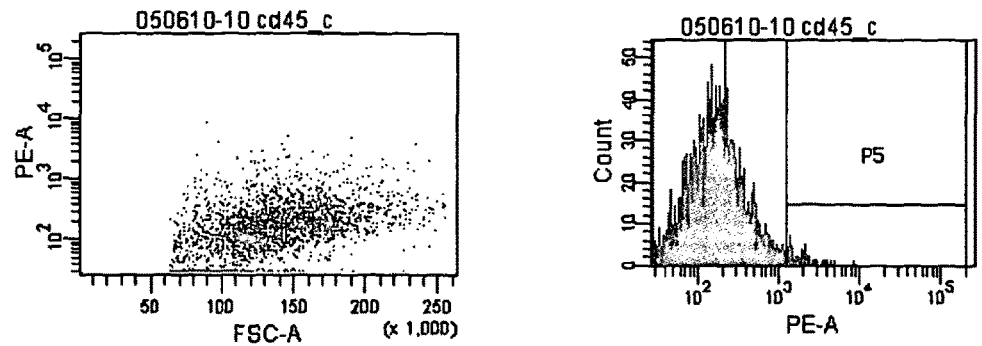
FIG. 15 depicts flow cytometry analysis of CD45 stained cells with FIG. 15A depicting an isotype control and FIG. 15B corresponding to pathway 3-8-9-7.
Figure 15B:
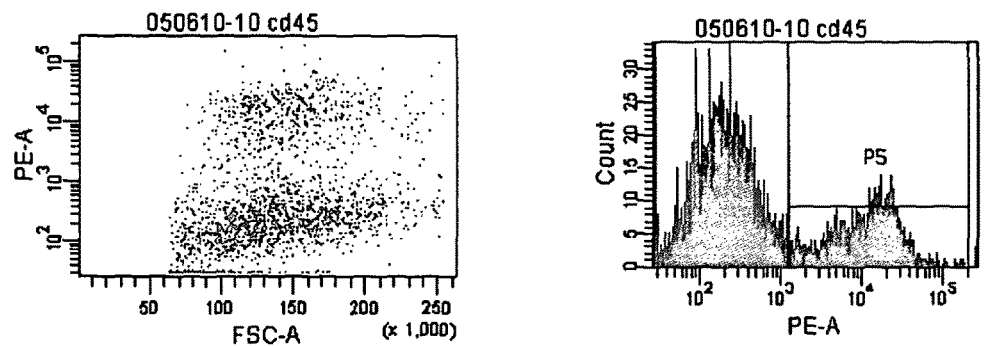

FIG. 15—flow cytometry analysis of CD45 stained cells with FIG. 15A depicting an isotype control (2.6% of population positive) and FIG. 15B corresponding to pathway 3-8-9-7 (28.8% of population positive).

Figure 16A:
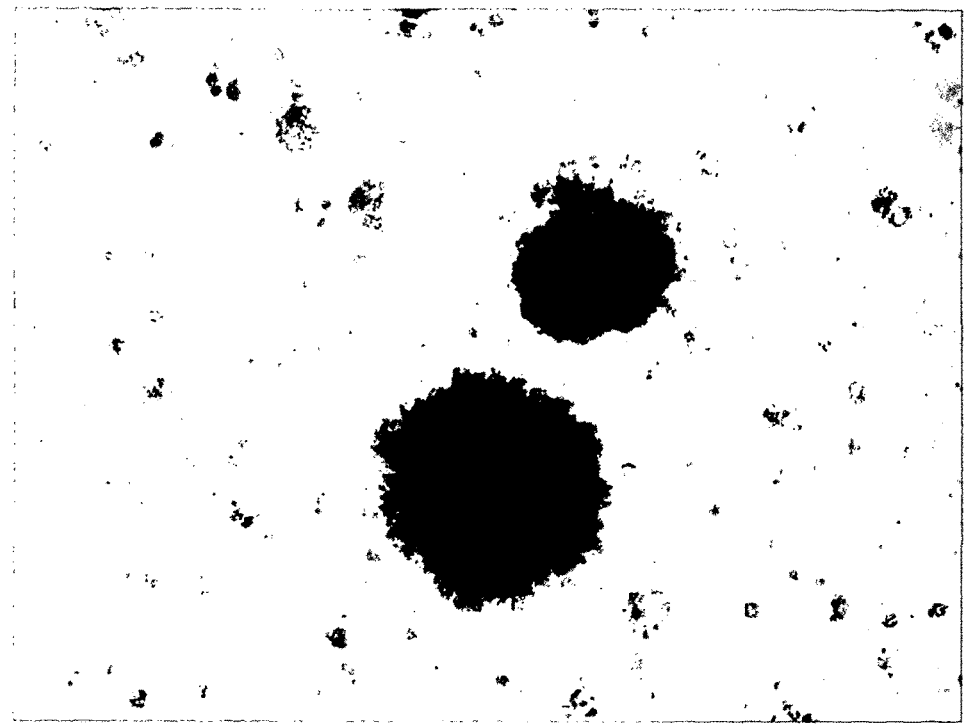
FIG. 16 corresponds to pathway 10-1-8-5 and shows two examples of B-lymphocyte type colonies.
Figure 16B:
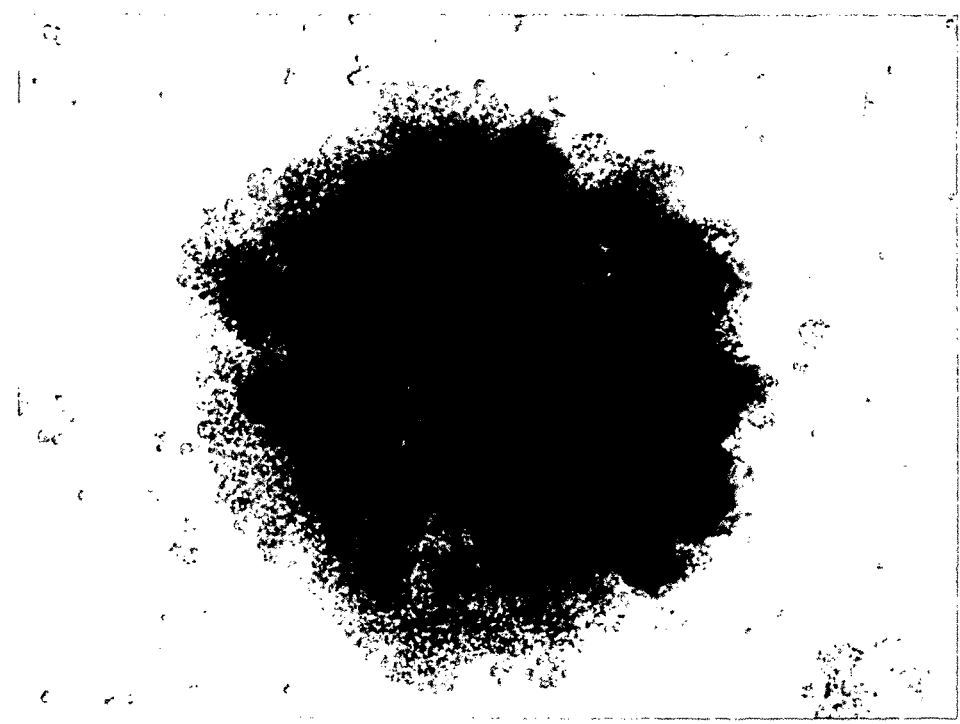

For cluster B, pathways from this cluster did not give monocytic, granulocytic and erytrocytic colonies semi-solid medium, but instead gave rise to B-lymphocyte type colonies in specially formulated semi-solid media containing Il-7 cytokine. This is illustrated in FIG. 16 for pathway 10-1-8-5, which shows two examples of B-lymphocyte type colonies.

Figure 17A:
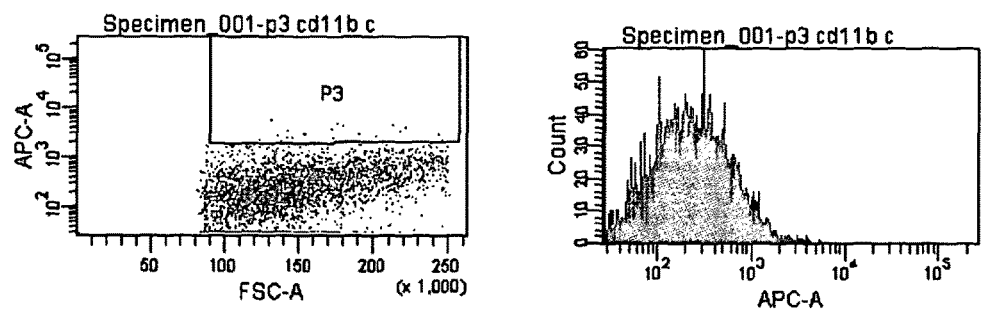
FIG. 17 depicts flow cytometry analysis of CD11b stained cells with FIG. 17A depicting an isotype control and FIG. 17B corresponding to pathway 10-1-8-5.
Figure 17B:
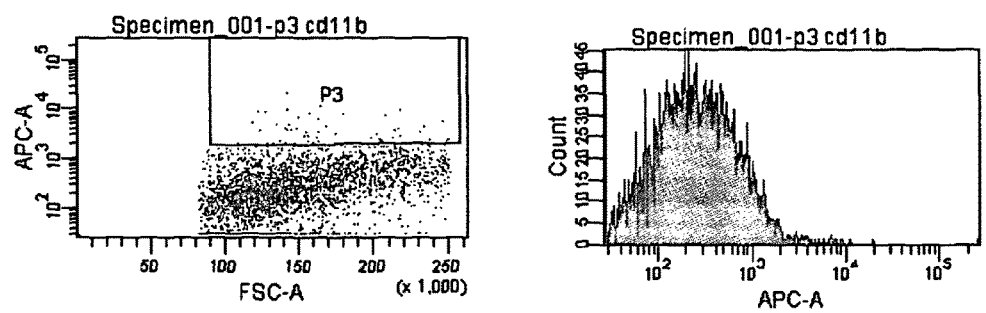

Cells produced by this pathway (10-1-8-5) were negative for myeloid marker CD11b and positive for lymphoid markers CD45R/B220, CD3e and CD49b, as shown in FIGS. 17-20. In particular, these Figures show:

FIG. 17—flow cytometry analysis of CD11b stained cells with FIG. 17A depicting an isotype control (0.6% of population positive) and FIG. 17B corresponding to pathway 10-1-8-5 (1.6% of population positive).

Figure 18A:
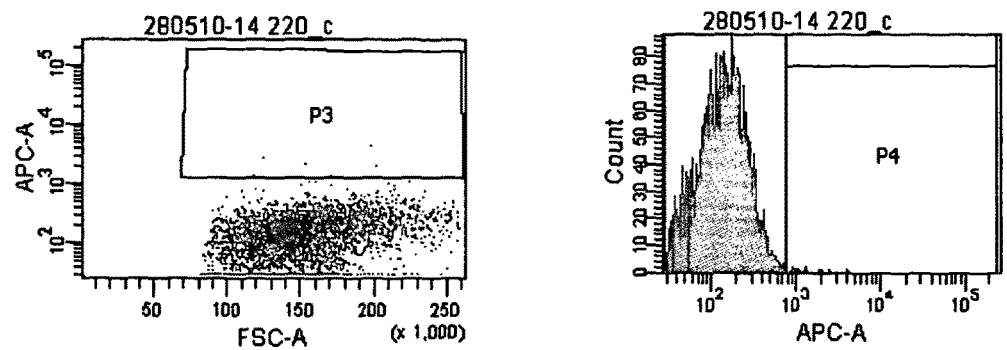
FIG. 18 depicts flow cytometry analysis of CD45r/b220 stained cells with FIG. 18A depicting an isotype control and FIG. 18B corresponding to pathway 10-1-8-5.
Figure 18B:
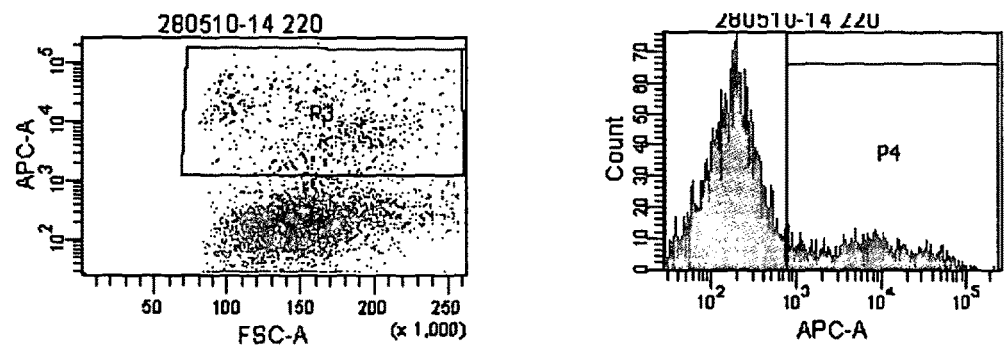

FIG. 18—flow cytometry analysis of CD45r/B220 stained cells with FIG. 18A depicting an isotype control (0.3% of population positive) and FIG. 18B corresponding to pathway 10-1-8-5 (21.7% of population positive).

Figure 19A:
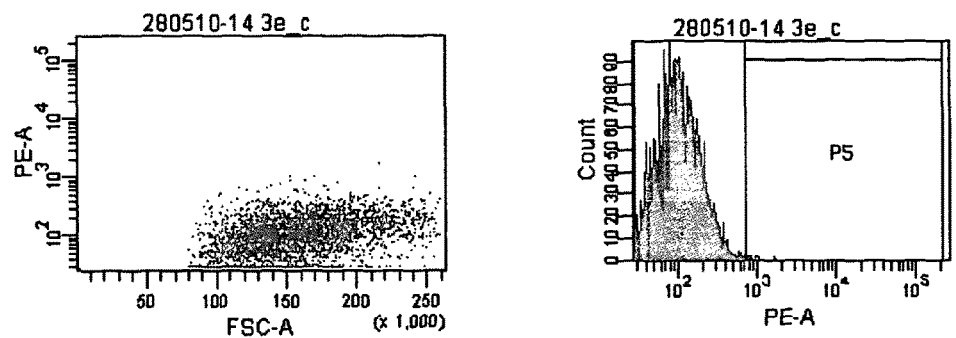
FIG. 19 depicts flow cytometry analysis of CD3e stained cells with FIG. 19A depicting an isotype control and FIG. 19B corresponding to pathway 10-1-8-5.
Figure 19B:
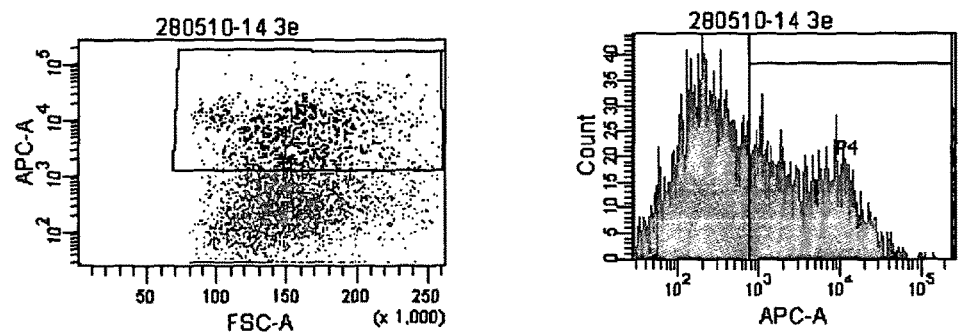

FIG. 19—flow cytometry analysis of CD3e stained cells with FIG. 19A depicting an isotype control (0.2% of population positive) and FIG. 19B corresponding to pathway 10-1-8-5 (41.6% of population positive).

Figure 20A:
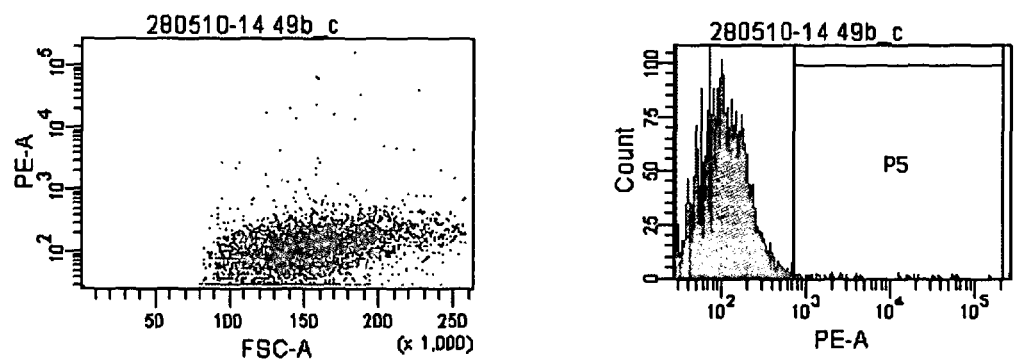
FIG. 20 depicts flow cytometry analysis of CD49b stained cells with FIG. 20A depicting an isotype control and FIG. 20B corresponding to pathway 10-1-8-5.
Figure 20B:
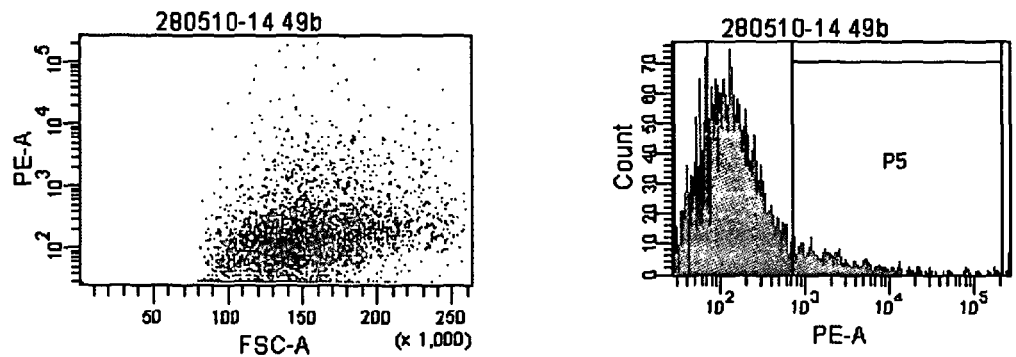

FIG. 20—flow cytometry analysis of CD49b stained cells with FIG. 20A depicting an isotype control (1.0% of population positive) and FIG. 20B corresponding to pathway 10-1-8-5 (9.9% of population positive).

It will be appreciated that cluster A therefore corresponds to one biological pathway from a hematopoietic stem cell, namely to a myeloid progenitor cell, while cluster B corresponds to a different biological pathway, namely to a lymphoid progenitor cell. Accordingly, grouping results as described herein not only helps to improve the identification of positive results from an experiment, but also helps to identify and discriminate between different types of positive result within a cell culture experiment. In particular, the grouping or clustering of results may reflect different positive outcomes of biological importance in a much more significant and helpful way than simply counting the number of positive outcomes for any given pathway.

Figure 21:
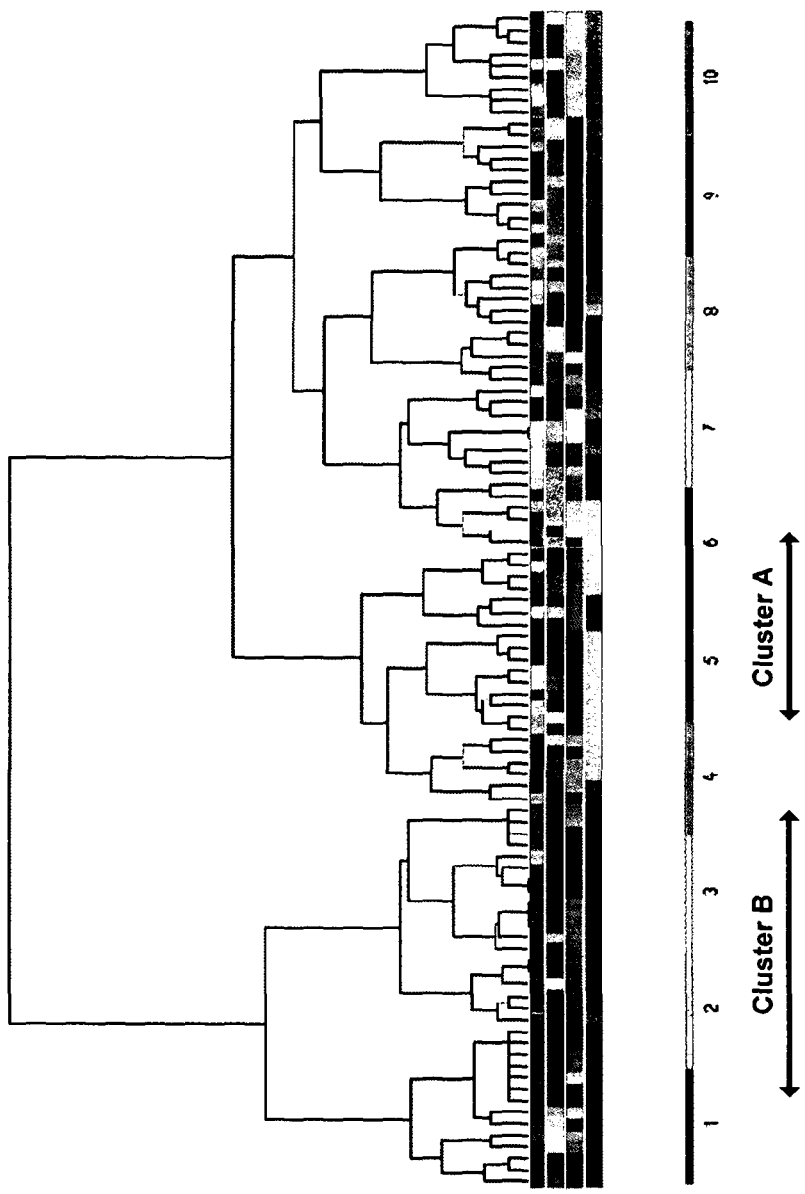
FIG. 21 is a diagram showing data from the experiment of FIG. 3 grouped using hierarchical clustering using Ward's method.

FIG. 21 is another representation of the experimental data from FIG. 3 using hierarchical clustering (as for FIGS. 5 and 7). The clustering for FIG. 21 was performed using Ward's method (sometimes referred to as Ward's linkage) to assemble the results into clusters. This technique is based on clustering objects to minimise variance—i.e. variance can be considered as the measure of distance for the clustering.

The band underneath the dendogram of FIG. 21 contains four strips, one corresponding to each round of treatment, with the first treatment at the top (adjacent the dendogram) and the fourth treatment at the bottom (furthest from the dendogram). Each strips is colour-coded to denote the particular treatment used in that round for that bead or sample—i.e. the treatments for a sample corresponding to a given branch of the dendrogram are represented by the four colours immediately below the branch, one from each strip. The bar at the bottom of the diagram provides a key relating each colour to the corresponding treatment number.

Also marked on FIG. 21 are cluster A and cluster B, which are the same two clusters as denoted likewise on the clustering shown in FIG. 7. In particular, cluster A corresponds to pathways AX-BX-C8/C9-D7, while cluster B corresponds to A10-B1-CX-D1/D5/D6 (or slightly more generally, A10-

B1-CX-DX). As discussed above, these two clusters differentiate cells into different phenotypes. The use of Ward's method for the hierarchical clustering has been found to provide an effective tool for the investigation and analysis of the cell culture data.

In summary, the above embodiments are provided by way of example only, and the skilled person will be aware of many potential modifications or variations that remain with the scope of the present invention as defined by the appended claims.

The invention claimed is:

1. A method comprising:
performing cell culture experiments comprising multiple stages of cell culture in succession on each sample from a large number of samples to obtain cell culture results, where each stage represents a cell culture treatment having a particular set of conditions, such that each sample follows a protocol specified by the identity and order of the treatments applied to the cell culture;
specifying a subset of the samples that yielded a desired cell culture outcome;
performing, by computer, an analysis of the results from the samples in the subset to produce an ordering or grouping of the results, wherein the analysis for producing the ordering or grouping utilises information on similarities between different protocols;
based at least in part on said ordering or grouping, identifying one or more protocols that are effective for obtaining the desired cell culture outcome; and
performing further cell culture experiments in which each sample follows a respective protocol selected from the one or more identified protocols that are effective for obtaining the desired cell culture outcome, such that cell culture treatments are applied to each sample in accordance with the identity and order of the cell culture treatments specified by the respective protocol selected for that sample.

2. The method of claim 1, wherein the analysis for producing the ordering or grouping further utilises the number of samples from the subset that follow each protocol.

3. The method of claim 1, wherein assessing the similarity between different protocols includes determining a distance measurement between the different protocols.

4. The method of claim 3, wherein determining a distance measurement between the different protocols includes counting the number of stages in common for the protocols concerned.

5. The method of claim 3, wherein the distance measurement provides a measure of treatment similarity within individual stages of the protocols.

6. The method of claim 1, wherein said analysis is performed on a data set comprising a record for each sample in the subset.

7. The method of claim 6, wherein each record comprises an identifier of the sample and information on the protocol applied to the sample.

8. The method of claim 7, wherein the information on the protocol applied to the sample comprises an ordered listing of the treatments applied to the sample.

9. The method of claim 8, wherein said ordered listing is represented as a binary string, wherein each bit in the binary string corresponds to a different treatment in a different stage, and the value of the bit indicates whether or not the treatment was applied to the sample for that particular stage.

10. The method of claim 1, wherein the grouping or ordering the results comprises clustering the results.

11. The method of claim 10, wherein said clustering comprises hierarchical clustering.

12. The method of claim 11, wherein said hierarchical clustering is based on Ward's linkage.

13. The method of claim 10, wherein said clustering comprises a self-organising map.

14. An apparatus comprising:
a cell culture facility for performing cell culture experiments comprising multiple stages of cell culture in succession on each sample from a large number of samples to obtain cell culture results, where each stage represents a cell culture treatment having a particular set of conditions, such that each sample follows a protocol specified by the identity and order of the treatments applied to the cell culture;
a memory for containing data specifying a subset of the samples that yielded a desired cell culture outcome; and
a processor configured to perform a computer-implemented analysis of the results from the samples in the subset:
to produce an ordering or grouping for the results, wherein the analysis for producing the ordering or grouping utilises information on similarities between different protocols;
to identify, based at least in part on said ordering or grouping, one or more protocols that are effective for obtaining the desired cell culture outcome; and
to perform further cell culture experiments in which each sample follows a respective protocol selected from the one or more identified protocols that are effective for obtaining the desired cell culture outcome, such that cell culture treatments are applied to each sample in accordance with the identity and order of the cell culture treatments specified by the respective protocol selected for that sample.

15. The apparatus of claim 14, wherein said apparatus comprises a cytometry system.

* * * * *